(12) United States Patent
Liang et al.

(10) Patent No.: US 7,643,655 B2
(45) Date of Patent: ***Jan. 5, 2010

(54) SYSTEM AND METHOD FOR ANIMAL SEIZURE DETECTION AND CLASSIFICATION USING VIDEO ANALYSIS

(75) Inventors: Yiqing Liang, Vienna, VA (US);
Vikrant Kobla, Ashburn, VA (US);
Xuesheng Bai, Fairfax, VA (US)

(73) Assignee: Clever Sys, Inc., Reston, VA (US)

( * ) Notice: Subject to any disclaimer, the term of this patent is extended or adjusted under 35 U.S.C. 154(b) by 554 days.

This patent is subject to a terminal disclaimer.

(21) Appl. No.: 11/329,573

(22) Filed: Jan. 11, 2006

(65) Prior Publication Data
US 2006/0110049 A1    May 25, 2006

Related U.S. Application Data

(63) Continuation-in-part of application No. 10/698,044, filed on Oct. 30, 2003, now Pat. No. 7,209,588, which is a continuation-in-part of application No. 09/718,374, filed on Nov. 24, 2000, now Pat. No. 6,678,413.

(51) Int. Cl.
*G06K 9/00* (2006.01)
*A01K 1/03* (2006.01)
(52) U.S. Cl. .................. 382/110; 382/224; 119/421
(58) Field of Classification Search .................. 382/100, 382/103, 106–110, 117, 118, 128, 129, 151, 382/156, 173, 174, 190, 203, 214, 243, 254, 382/256, 302, 305, 286; 424/185.1, 158.1; 435/325; 119/421; 514/282; 348/143; 702/141
See application file for complete search history.

(56) References Cited

U.S. PATENT DOCUMENTS

| | | | |
|---|---|---|---|
| 3,100,473 | A | 8/1963 | Kissel |
| 3,304,911 | A | 2/1967 | Hakata et al. |
| 3,485,213 | A | 12/1969 | Scanlon |
| 3,803,571 | A | 4/1974 | Luz |
| 3,974,798 | A | 8/1976 | Meetze, Jr. |
| 4,337,726 | A | 7/1982 | Czekajewski et al. |
| 4,574,734 | A | 3/1986 | Mandalaywala et al. |
| 4,600,016 | A | 7/1986 | Boyd et al. |

(Continued)

FOREIGN PATENT DOCUMENTS

EP        363755 A2    4/1990

(Continued)

OTHER PUBLICATIONS

Allen, William H. "Animals and their Models do their Locomotions: Biologists Probe Mechanics and Energetics of Animal Motion". Jun. 1995. Biosciences. vol. 45, No. 6, pp. 381-383.

(Continued)

*Primary Examiner*—Seyed Azarian
(74) *Attorney, Agent, or Firm*—Alston & Bird LLP

(57) ABSTRACT

A system and method for analyzing video images including images of an animal to detect and classify seizure behavior of the animal. Seizure-salient features are detected from identified postures and identified movements of body parts of the animal. The seizure-salient features are used to detect and classify the occurrences of seizures.

36 Claims, 14 Drawing Sheets

U.S. PATENT DOCUMENTS

| | | | |
|---|---|---|---|
| 4,631,676 | A | 12/1986 | Pugh |
| 4,888,703 | A | 12/1989 | Baba et al. |
| 5,299,454 | A | 4/1994 | Fuglewicz et al. |
| 5,428,723 | A | 6/1995 | Ainscow et al. |
| 5,546,439 | A | 8/1996 | Hsieh |
| 5,581,276 | A | 12/1996 | Cipolla et al. |
| 5,596,994 | A | 1/1997 | Bro |
| 5,708,767 | A | 1/1998 | Yeo et al. |
| 5,748,775 | A | 5/1998 | Tsuchikawa et al. |
| 5,816,256 | A | 10/1998 | Kissinger et al. |
| 5,821,945 | A | 10/1998 | Yeo et al. |
| 5,870,138 | A * | 2/1999 | Smith et al. ............... 348/143 |
| 6,010,465 | A | 1/2000 | Nashner |
| 6,061,088 | A | 5/2000 | Khosravi et al. |
| 6,072,496 | A | 6/2000 | Guenter et al. |
| 6,072,903 | A | 6/2000 | Maki et al. |
| 6,081,607 | A | 6/2000 | Mori et al. |
| 6,088,468 | A | 7/2000 | Ito et al. |
| 6,144,366 | A | 11/2000 | Numazaki et al. |
| 6,212,510 | B1 | 4/2001 | Brand |
| 6,231,527 | B1 | 5/2001 | Sol |
| 6,242,456 | B1 * | 6/2001 | Shuster et al. ............. 514/282 |
| 6,263,088 | B1 | 7/2001 | Crabtree et al. |
| 6,295,367 | B1 | 9/2001 | Crabtree et al. |
| 6,311,644 | B1 | 11/2001 | Pugh |
| 6,365,621 | B1 * | 4/2002 | Tanaka et al. ............. 514/423 |
| 6,468,998 | B1 | 10/2002 | Kuroita et al. |
| 6,535,131 | B1 | 3/2003 | Bar-Shalom et al. |
| 6,576,237 | B1 | 6/2003 | Ingham et al. |
| 6,601,010 | B1 | 7/2003 | Fowler et al. |
| 6,630,148 | B1 | 10/2003 | Ingham et al. |
| 6,630,347 | B1 | 10/2003 | Huang et al. |
| 6,650,778 | B1 | 11/2003 | Matsugu et al. |
| 6,658,287 | B1 * | 12/2003 | Litt et al. .................... 600/544 |
| 6,678,413 | B1 | 1/2004 | Liang et al. |
| 6,704,502 | B2 | 3/2004 | Morofuji |
| 6,715,444 | B1 | 4/2004 | Yabusaki et al. |
| 6,757,444 | B2 | 6/2004 | Matsugu et al. |
| 6,819,796 | B2 | 11/2004 | Hong et al. |
| 6,837,184 | B2 | 1/2005 | Gondhalekar et al. |
| 6,899,686 | B2 | 5/2005 | Hampton et al. |
| 6,941,239 | B2 * | 9/2005 | Unuma et al. ............... 702/141 |
| 7,133,537 | B1 | 11/2006 | Reid |
| 7,269,516 | B2 * | 9/2007 | Brunner et al. ............. 702/19 |
| 2003/0024482 | A1 | 2/2003 | Gondhalekar et al. |
| 2003/0100998 | A2 | 5/2003 | Brunner et al. |
| 2004/0009845 | A1 | 1/2004 | Johnson |
| 2004/0020443 | A1 | 2/2004 | Ohl |
| 2004/0141636 | A1 | 7/2004 | Liang et al. |

FOREIGN PATENT DOCUMENTS

| | | |
|---|---|---|
| EP | 0 933 726 A2 | 8/1999 |
| JP | 63-133061 A | 6/1988 |
| JP | 08-063603 A | 3/1996 |
| JP | 08-240830 A | 9/1996 |
| JP | 09-0735541 A | 3/1997 |
| JP | 09-251441 A | 9/1997 |
| JP | 11-052215 A | 2/1999 |
| JP | 11-259643 A | 9/1999 |
| JP | 11-296651 A | 10/1999 |
| JP | 2000-215319 A | 8/2000 |
| WO | WO02/43352 | 5/2002 |

OTHER PUBLICATIONS

Birch et al. 2001. "A miniature Hybrid Robot Propelled by Legs". Proceedings of the 2001 IEE/RSJ International Conference on Intelligent Robots and Systems, p. 845-851.

Clarke, K.A. and J. Still "Development and consistency of gait in the mouse" Physiology & Behavior 73:159-164 (2001).

Clarke, K.A. and J. Still "Gait Analysis in the Mouse" Physiology & Behavior 66(5):723-729 (1999).

Crnic, L.S.; "Effects Of Infantile Undernutrition On Adult Learning In Rats: Methodological And Design Problems"; Psychological Bullentin; vol. 83; No. 4; 1976; pp. 715-728.

Gurney, Mark E. et al. "Motor Neuron Degeneration in Mice That Express a Human Cu,Zn Superoxide Dismutase Mutation" Science 264:1772-1775 (Jun. 17, 1994).

Kram, R., Wong, B. and Full, R.J. 1997. "Three-Dimensional Kinematics and Limb Kinetic Energy of Running Cockroaches". The Journal of Experimental Biology 200, 1919-1929.

Liang, Yiqing, "Digital Video Technologies and Their Applications," Beijing Dec. 2000, 24 pages.

Macmillan, D.L. "A Physiological Analysis of Walking in the American Lobster". Feb. 6, 1975. Biological Sciences (England) vol. 270.

Ozer, I. Burak et al., "Human Detection in Compressed Domain." Proceedings of International Conference on Image Processing, Thessaloniki, Greece, Oct. 2001.

Ozer, W. Wolf et al., "Video Analysis For Smart Rooms," Proc. SPIE vol. 4519, p. 84-90, Internet Multimedia Management Systems II, Jul. 2001.

Wolf, Wayne et al., "A Smart Camera for Real-Time Human Activity Recognition," 2001 IEEE Workshop on Signal Processing Systems, Antwerp, Belgium, Sep. 2001.

Philips, Michael et al.; "Video Segmentation Techniques For News"; SPIE, vol. 2916; 1996; pp. 243-251.

Wolf, Wayne; "Hidden Markov Model Parsing Of Video Programs"; IEEE; 1997; pp. 2609-2611.

Crnic, Linda S. et al.; "Automated Analysis of Digitized Videotapes of Mouse Home-Cage Behavior"; 2000 Neuroscience Annual Conference, New Orleans; Oct. 2000; (1pg).

Crnic, Linda S. et al.; "Automated Analysis of Digitized Videotapes of Mouse Home-Cage Behavior"; Symposium of Behavioral Phenotyping of Mouse Mutants, Cologne, Germany; Feb. 17-19, 2000; (1pg).

Liang, Yiqing et al.; "Multiple Motion Detection Using Genetic Algorithms"; DARPA Image Understanding Workshop, Monterey, CA; Nov. 1998; (8pgs).

Liang, Yiqing et al; "A Shot Boundary Detection Algorithm Adapted For Predator Video"; Applied Imagery and Pattern Recognition (AIPR) '98; Washington, D.C.; Oct. 1998; (9pgs).

Zeng, H. et al; "Data Mining For Combat Vehicle Classification Using Machine Learning"; Applied Imagery and Pattern Recognition (AIPR) '98, Washington, D.C.; Oct. 1998; (10pgs).

Liang Yiqing et al.; "A Ground Target Detection System For Digital Video Database"; Conference on Visual Information Processing VII, AeroSense '98, Orlando, Florida; Apr. 1998; (6pgs).

Liang, Yiqing et al.; "A Practical Video Indexing and Retrieval System"; Applied Imagery and Pattern Recognition (AIPR) '97, Washington, D.C.; Oct. 1997; (8pgs).

Liang, Yiqing et al; "A Practical Video Database Based on Language and Image Analysis"; AAAI Technical Report, SS-97-03,, ed., Alex Hauptmann & Michael Witbrock, Intelligent Use And Integration Of Text, Image, Video and Speech; Mar. 1997; (6pgs).

Wolf, Wayne et al.; "A Digital Video Library for Classroom Use"; International Conference on Digital Library '95, Tsukuba; Aug. 1995; (6pgs).

Wolf, Wayne et al.; "A Digital Video Library On The World Wide Web"; ACM Multimedia '96, Addison-Wesley, Publishing Company; Nov. 1996; pp. 433-434.

Liang, Yiqing et al.; "Apprenticeship Learning of Domain Models"; Seventh Intl. Conference On Software Engineering And Knowledge Engineering, Rockville, Maryland; Jun. 1995; (9pgs).

Liu, Bede et al.; "The Princeton Video Library of Politics"; Digital Libraries '94, Texas A & M University; Jun. 1994; pp. 215-216.

Palmer, James D. et al.; "Classification As An Approach To Requirements Analysis"; 1.sup.st ASIS SIG/CR Classification Research Workshop, Toronto, Canada; Nov. 4, 1990; pp. 129-136.

Palmer, James D. et al., "Approaches to Domain Model Construction", Domain Modeling Workshop, 13.sup.th International Conference on Software Engineering, Austin, Texas; Mar. 26, 1991; pp. 130-135.

Schrott, Lisa M. et al., "Sensitivity To Foot Shock In Autoimmune NZB .times. NZW F1 Hybrid Mice"; Physiology & Behavior; vol. 56; No. 5; 1994; pp. 849-853.

Coussons-Read, Mary E. et al.; "Behavioral Assessment Of The Ts65Dn Mouse, A Model For Down Syndrome: Altered Behavior In The Elevated Plus Maze And Open Field"; Behavior Genetics; vol. 26; No. 1; 1996; pp. 7-13.

Schrott, Lisa M. et al.; "Increased Anxiety Behaviors In Autoimmune Mice"; Behavioral Neuoscience; vol. 110; No. 3; 1996; pp. 492-502.

Schrott, Lisa M. et al.; "The Role Of Performance Factors In The Active Avoidance-Conditioning Deficit In Autoimmune Mice"; Behavioral Neuroscience; vol. 110; No. 3; 1996; pp. 486-491.

Schrott, Lisa M. et al.; "Anxiety Behavior, Exploratory Behavior, And Activity In NZB .times. NZW F1 Hybrid Mice: Role Of Genotype And Autoimmune Disease Progression"; Brain, Behavior And Immunity; vol. 10; 1996; pp. 260-274.

Schrott,, Lisa M. et al.; "Attenuation Of Behavioral Abnormalities In Autoimmune Mice By Chronic Soluble Interferon-. gamma. Receptor Treatment"; Brain, Behavior And Immunity; vol. 12; 1998; pp. 90-106.

Sakic, Boris et al.; "Reduced Corticotropin-Releasing Factor And Enhanced Vasopressin Gene Expression In Brains Of Mice With Autoimmunity-Induced Behavioral Dysfunction"; Journal Of Neuroimmunology 96; 1999; pp. 80-91.

Crnic, L.S. et al.; "Down Syndrome: Neuropsychology And Animal Models"; Progress in Infancy Research; vol. 1; 2000; pp. 69-111.

Granholm, Ann-Charlotte et al.; "Loss of Cholinergic Phenotype in Basal Forebrain Coincides With Cognitive Decline In A Mouse Model of Down's Syndrome"; Experimental Neurology; vol. 161; 2000; pp. 647-663.

Sago, Haruhiko et al.; "Genetic Dissection Of Region Associated With Behavioral Abnormalities In Mouse Models For Down Syndrome"; Pediatric Research; vol. 48; No. 5; 2000; pp. 606-613.

Hyde, L.A. et al.; "Ts65Dn Mice, A Model For Down Syndrome, Have Deficits In Context Discrimination Learning Suggesting Impaired Hippocampal Function"; Behavioral Brain Research; vol. 118; 2001; pp. 53-60.

Hyde, L.A. et al.; "Motor Learning in Ts65Dn Mice, A Model For Down Syndrome"; Developmental Psychobiology; vol. 38; 2001; pp. 33-45.

Nielsen, D.M. et al.; "Elevated Plus Maze Behavior, Auditory Startle Response,, And Shock Sensitivity In Predisease And In Early Stage Autoimmune Disease MRL/lpr Mice"; Brain Behavior And Immunity; 2001; pp. 1-16.

Hyde, L.A. et al.; "Age-Related Deficits In Context Discrimination Learning In Ts65Dn Mice That Model Down Syndrome And Alzheimer's Disease"; Behavioral Neuroscience; vol. 115; 2001; pp. 1-8.

Crnic, L.S.; "Effects Of Infantile Undernutrition On Adult Learning In Rats: Methodological And Design Problems"; Psychological Bullentin; vol. 83; No. 4; 1976; pp. 715-728.

Crnic, L.S.; "Transgenic And Null Mutant Animals For Psychosomatic Research"; Psychosomatic Medicine; vol. 58; 1996; pp. 622-632.

Dierssen, Mara et al.; "Murine Models For Down Syndrome"; Physiology And Behavior; vol. 73; 2001; pp. 859-871.

Cohen, J.J. et al.; "Behavior, Stress, and Lymphocyte Recirculation"; Stress, Immunity And Aging; 1984; pp. 73-80.

Crnic, L.S.; "Early Experience Effects: Evidence For Continuity?"; Continuities And Discontinuities In Development, Plenum Press, New York; 1984; pp. 355-368.

Crnic, L.S. et al.; "Animal Modes Of Human Behavior: Their Application To The Study Of Attachment"; The Development of Attachment And Affiliative Systems: Neurobiological And Psychobiological Aspects, Plenum, New York; 1982; pp. 31-42.

Crnic, L.S.; "Animal Models Of Early Malnutrition: A Comment On Bias, Dependability, And Human Importance"; Malnutrition And Behavior: Critical Assessment Of Key Issues; 1984; pp. 460-468.

Kobla, Vikrant et al.; "Detection Of Slow-Motion Replay Sequences For Identifying Sports Videos"; In Proceedings Of IEEE Third Workshop On Multimedia Signal Processing (MMSP); Sep. 1999; (6pgs).

Dorai, C. et al.; "Generating Motion Descriptors From MPEG-2 Compressed HDTV Video For Content-Based Annotation And Retrieval"; In Proceedings Of IEEE Third Workshop On Multimedia Signal Processing (MMSP); Sep. 1999; (4pgs).

Kobla, Vikrant et al.; "Identifying Sports Videos Using Replay, Text, And Camera Motion Features"; Proceedings Of The SPIE Conference On Storage And Retrieval For Media Databases; vol. 3972; Jan. 2000; (12pgs).

Liang, Yiqing et al.; "Toward An Object And Multiple-Modalities Based Indexing And Retrieval Of Video Contents"; DARPA's Image Understanding Workshop; Monterey, California; Nov. 1998; (21pgs).

Liang, Yiqing; "A Practical Digital Video Database Based On Language And Image Analysis"; International Conference Multimedia Databases On Internet; Seoul, Korea; Oct. 10, 1997; (23pgs).

Yu, Hong-Heather et al; "A Visual Search System For Video And Image Databases"; In Proceedings, ICMCS 1997, IEEE Computer Society Press; 1997; pp. 517-524.

Yu, Hong-Heather et al.; "Multi-Resolution Video Segmentation Using Wavelet Transformation"; In Storage And Retrieval For Image And Video Databases VI, SPIE; vol. 3312; 1998; pp. 176-187.

Yu, Hong-Heather et al.; "A Hierarchical Multiresolution Video Shot Transition Detection Scheme"; Computer Vision And Image Understanding; vol. 75; Jul./Aug. 1999; pp. 196-213.

Li, Yanbing et al; "Semantic Image Retrieval Through Human Subject Segmentation And Characterization"; In Storage And Retrieval For Image And Video Databases V, SPIE; vol. 3022; 1997; pp. 340-351.

Yu, Hong-Heather et al; "A Multi-Resolution Video Segmentation Scheme For Wipe Transition Identification"; In Proceedings IEEE ICASSP; vol. 5; 1998; pp. 2965-2968.

Liang, Yiqing Ph.D.; "Video Retrieval Based On Language And Image Analysis"; Defense Advanced Research Projects Agency Information Systems Office; May 28, 1999; 35 pgs.

Crnic, L.S.; "The Effects Of Chronic Lithium Chloride Administration On Complex Schedule Performance, Activity, And Water Intake In The Albino Rat"; Physiological Psychology; vol. 4; 1976; pp. 166-170.

Crnic, L.S.; "Maternal Behavior In The Undernourished Rate (*Rattus norvegicus*)"; Physiology & Behavior; vol. 16; 1976; pp. 677-680.

Crnic, Linda S. et al., "Automated Analysis of Digitized Videotapes of Mouse Home-Cage Behavior", Feb. 17, 2000.

Crnic et al. "Automated Analysis of Digitized Videotapes of Mouse Home-Cage Behavior," Program No. 573.7 2000Neuroscience Meeting Planner, New Orleans, LA Society of Neuroscience, (Nov. 7, 2000).

Brand M. et al. "Discovery and segmentation of Activities in Video," IEEE Transactions on Pattern Analysis and Machine Intelligence, IEEE Service Center, Los Alamitos, CA US, vol. 22, No. 8, pp. 844-851, (Aug. 1, 2000).

Stauffer et al. "Learning Patterns of Activity Using Real-Time Tracking," IEEE Transactions on Pattern Analysis and Machine Intelligence, IEEE Service Center, Los Alamitos, CA US, vol. 22, No. 8, pp. 747-757, (Aug. 1, 2000).

Rota et al. "Video Sequence Interpretation for Visual Surveillance," Proceedings, IEEE Workshop on Visual Surveillance, vol. 3rd, pp. 59-67, (Jul. 1, 2000).

Crnic, L.S.; "Effects Of Infantile Undernutrition On Adult Sucrose Solution Consumption In The Rat"; Physiology & Behavior; vol. 22; 1979; pp. 1025-1028.

Crnic, L.S.; "Models Of Infantile Malnutrition In Rats: Effects On Maternal Behavior"; Developmental Psychobiology; vol. 13; 1980; pp. 615-628.

Crnic, L.S. et al.; "Separation-Induced Early Malnutrition: Maternal, Physiological And Behavioral Effects"; Physiology & Behavior; vol. 26; 1981; pp. 695-706.

Crnic, L.S.; "Effects Of Nutrition And Environment On Brain Biochemistry And Behavior"; Developmental Psychobiology; vol. 16; 1983; pp. 129-145.

Crnic, L.S. et al.; "Behavioral Effects Of Neonatal Herpes Simplex Type 1 Infection Of Mice"; Neurotoxicology and Teratology; vol. 10; 1988; pp. 381-386.

Segall, M.A. et al.; "An Animal Model For The Behavioral Effects Of Interferon"; Behavioral Neuroscience; vol. 104; No. 4; 1990; pp. 612-618.

Segall, M.A. et al.; "A Test Of Conditioned Taste Aversion With Mouse Interferon-.alpha."; Brain, Behavior And Immunity; vol. 4; 1990; pp. 223-231.

Crnic, L.S. et al.; "Prostaglandins Do Not Mediate Interferon-.alpha. Effects On Mouse Behavior"; Physiology & Behavior; vol. 51; 1992; pp. 349-352.

Crnic, L.S. et al.; "Behavioral Effects Of Mouse Interferons-.alpha. and -.gamma. And Human Interferon-.alpha. In Mice"; Brain Research; vol. 590; 1992; pp. 277-284.

Dunn, Andrea L. et al.; "Repeated Injections Of Interferon-.alpha. A/D In Balb/c Mice: Behavioral Effects"; Brain, Behavior, And Immunity; vol. 7; 1993; pp. 104-111.

Ozer, I. Burak et al.; "Relational Graph Matching For Human Detection And Posture Recognition"; SPIE, Photonic East 2000, Internet Multimedia Management Systems, Boston; Nov. 2000; (12pgs).

Ozer, I. Burak et al.; "A Graph Based Object Description For Information Retrieval In Digital Image And Video Libraries"; Proceedings of IEEE Workshop on Content-Based Access Of Image & Video Libraries, Colorado; Jun. 1999; (5pgs).

Yu, H. et al.; "A Visual Search System For Video And Image Databases"; IEEE Multimedia; 1997; (8pgs).

Yu, H. et al.; "Hierarchical, Multi-Resolution Algorithms For Dictionary-Driven Content-Based Image Retrieval"; International Conference On Image Processing; 1997; (4pgs).

Wolf, W.; "Key Frame Selection By Motion Analysis"; Proceedings, ICASSP, IEEE Press; 1996; (4pgs).

Philips, Michael et al.; "A Multi-Attribute Shot Segmentation Algorithm For Video Programs"; Proceedings, SPIE 2916; 1996; (10pgs).

Yeung, Minerva M. et al.; "Video Browsing Using Clustering And Scene Transitions on Compressed Sequences"; SPIE Conference on Multimedia Computing And Networking; vol. 2417, 1995; pp. 399-413.

Yu, H. et al.; "Scenic Classification Methods For Image And Video Databases"; SPIE; vol. 2606; 1995; pp. 363-371.

Yeo, B.L. et al.; "Theft-Resistant Video Browsing Using Filtered Versions Of Compressed Sequences"; IEEE Conference On Multimedia Computing And Systems; 1995; (6pgs).

Ozer, I. Burak et al.; "Human Activity Detection In MPEG Sequence"; Proceedings Of IEEE Workshop On Human Motion,, Austin; Dec. 2000; pp. 61-66.

Kobla, Vikrant et al.; "Compressed Domain Video Segmentation"; CFAR Technical Report CS-TR-3688, University of Maryland, College Park; Oct. 25, 1996; (34pgs).

Kobla, Vikrant et al.; "Feature Normalization For Video Indexing And Retrieval"; CFAR Technical Report CS-TR-3732, University of Maryland, College Park; Nov. 1996; (40pgs).

Kobla, Vikrant et al.; "Archiving, Indexing, And Retrieval Of Video In The Compressed Domain"; In Proceedings Of SPIE Conference On Multimedia Storage And Archiving Systems; vol. 2916; Nov. 1996; (12pgs).

Kobla, Vikrant et al.; "Compressed Domain Video Indexing Techniques Using DCT And Motion Vector Information In MPEG Video"; In Proceedings of SPIE Conference On Storage And Retrieval For Image And Video Databases V; vol. 3022; Feb. 1997; (12pgs).

Kobla, Vikrant et al.; "Extraction Of Features For Indexing MPEG-Compressed Video"; In Proceedings of IEEE First Workshop On Multimedia Signal Processing (MMSP); Jun. 1997; (6pgs).

Kobla, Vikrant et al.; "Video Trails: Representing And Visualizing Structure In Video Sequences"; In Proceedings Of ACM Multimedia Conference; Nov. 1997; (12pgs).

Kobla, Vikrant et al.; "Developing High-Level Representations Of Video Clips Using Video Trails"; In Proceedings Of SPIE Conference On Storage And Retrieval For Image And Video Databases VI; Jan. 1998; (12pgs).

Kobla, Vikrant et al.; "Indexing And Retrieval Of MPEG Compressed Video"; Journal of Electronic Imaging; vol. 7(2); Apr. 1998; (36pgs).

Kobla, Vikrant et al.; "Special Effect Edit Detection Using Video Trails: A Comparison With Existing Techniquess"; Proceedings Of SPIE Conference On Storage And Retrieval For Image And Video Databases VII; Jan. 1999; (12pgs).

Dorai, C. et al; "Extracting Motion Annotations From MPEG-2 Compressed Video For HDTV Content Management Applications"; IEEE International Conference On Multimedia Computing And Systems; Jun. 1999; (6pgs).

Crnic, L.S.; "Nutrition And Mental Development"; American Journal of Mental Deficiency; vol. 88; No. 5; 1984 pp. 526-533.

Jones, A.P. et al.; "Maternal Mediation Of The Effects Of Malnutrition"; The Handbook Of Behavioral Teratology; Plenum; 1986; pp. 409-425.

Crnic, L.S.; "The Use of Animal Models To Study Effects Of Nutrition On Behavior"; Diet And Behavior: A Multidisciplinary Approach; Springer-Verlag; 1990; pp. 73-87.

Crnic, L.S.; "Behavioral Consequences Of Virus Infection"; Psychoneuroimmunology, Second Edition; Academic Press; 1991; pp. 749-769.

Crnic, L.S. et al.; "Animal Models Of Mental Retardation: An Overview"; Mental Retardation And Developmental Disabilities Research Reviews; vol. 2; 1996; pp. 185-187.

HVS Image Homepage Nov. 25, 1997; Video tracking system for Morris water maze, open field, radial-arm maze, etc.

AccuScan on-line catalog, Nov. 19, 1997.

Omnitech Electronics, Inc., Residential Maze Computerized System, 1991.

Omnitech Electronics, Inc., Olympus 1 Meter .times. 1 Meter Animal Activity Monitor, 1988.

Digiscan Optical Animal Activity Monitoring System, AccuScan Instruments, Inc., 1997.

Digiscan DMicro System; AccuScan Instruments, Inc., 1996.

Tremorscan Monitor Model TS1001; AccuScan Instruments, Inc., 1997.

"RotoScan" Rotometer High Resolution Rotation Monitoring; AccuScan Instruments, Inc., 1993.

Automated Plus Maze Open/Closed Arm System; AccuScan Instruments, Inc., 1991.

Digiscan Model CCDIGI Optical Animal Activity Monitoring System, AccuScan Instruments, Inc., 1997.

San Diego Instruments Behavioral Testing Systems, Nov. 19, 1997 (18 pages).

Ozer, I.B., et al., "Human Activity Detection in MPEG Sequences," Proceedings of IEEE Workshop on Human Motion, Austin, Texas, Dec. 7-8, 2000.

Fitzgerald, R.E. et al., "Validation of a Photobeam System for Assessment of Motor Activity In Rats," Toxicology, 49 (1988) pp. 433-439.

The Observer, Professional system for collection, analysis and management of observational data, Noldus Information Technology, 1996.

EthoVision, computer vision system for automation of behavioral experiments, Noldus Information Technology, 1997.

* cited by examiner

SYSTEM AND METHOD FOR ANIMAL SEIZURE DETECTION AND CLASSIFICATION USING VIDEO ANALYSIS

CROSS-REFERENCE TO RELATED APPLICATIONS

This application is a continuation-in-part of U.S. patent application Ser. No. 10/698,044, filed on Oct. 30, 2003 now U.S. Pat. No. 7,209,588, which is a continuation-in-part of U.S. patent application Ser. No. 09/718,374, filed on Nov. 24, 2000, now U.S. Pat. No. 6,678,413. The disclosures of these related applications are hereby incorporated by reference in their entirety.

FIELD OF THE INVENTION

This invention relates generally to analysis of animal behavior, and more particularly to detection and classification of animal seizure activity using video analysis.

BACKGROUND

Animals, including mice and rats, are used extensively as human models in research, for example the research of drug development, genetic functions, toxicology, and the understanding and treatment of diseases. Despite the differing lifestyles of humans and animals, their extensive genetic and neuro-anatomical similarities give rise to a wide variety of behavioral processes that are largely shared between species. Exploration of these shared brain functions sheds light on fundamental elements of human behavioral regulation.

Many behavioral test experiments have been designed for animals such as mice and rats to explore their behaviors. These experiments includes, but are not limited to, observation of home cage behaviors, open field locomotion experiments, object recognition experiments, maze experiments, freezing experiments for conditioned fear, gait analysis experiments, and monitoring of disease states such as cancer and epilepsy. In many cases these experiments use human observation of video of the experiment sessions, which often produces subjective and inaccurate results. Experiments using human observations are labor-intensive and thus expensive.

Over the last two decades major technological advances have enabled scientists to build a rich repository of rat and/or mouse models for epilepsy research. Scientists have generated numerous models of damage-induced epilepsy. In particular, systemic or focal-intercranial injection of substances such as kainic acid, tetanus toxin, pilocarpine, and other agents is known to cause a long-term or even permanent state of epileptic seizures. In these different models, the behaviors during the seizures have many similarities to human temporal lobe epilepsy, and furthermore, the electrophysical and histopathological abnormalities also have similarities.

These animal models are essential in the process of developing anti-epileptic drugs (AEDs). Currently, most researchers use animals from these models that exhibit seizures and either administer drugs or make other changes to the animal to see if the epileptic activity patterns are altered. This requires techniques that can measure the number, frequency, and types of occurring seizures.

Many current seizure detection systems involve using an electroencephalogram (EEG) for recording information, and using algorithms that can detect specific patterns in these EEG signals. Significant effort has been put into the research and development of EEG technology, and EEG signals can be accurately and automatically recorded. Improvements in EEG technology that have been made in recent years include radio telemetry technology that allows signals acquired by electrodes to be transmitted without tethers, and software that automatically analyzes EEG epileptiforms, determines the occurrences of seizures, and classifies the type of epilepsy.

However, using recorded EEG signals to detect seizures has important technical and conceptual problems. These problems include time-consuming and sophisticated surgery to implant electrodes into animals' brains, and the electrodes could have mechanical failures, causing significant alterations in the animals' behaviors or even sudden death of the animals. Noise in the EEG signals is also a drawback. Certain motor activity in an animal can cause severe noise in the EEG signals that needs to be filtered out. Sometimes, if this noise-causing activity is very similar to seizure activity, there will be no means of verifying occurrence of a seizure unless a video record is present.

When radio-telemetry of EEG signals is used, bandwidth becomes an issue as the sampling rate of the EEG signals that can be transmitted in limited to a few hundred hertz, compared to a standard rate of two kilohertz when using a tether. Another drawback with a radio-telemetry system is that multiple signals in the same room may interfere and lead to noisy data collection.

Finally, the software for detecting and classifying epileptic seizures in animals using EEG signals has not matured, with a precision of only fifty to sixty percent after twenty years of development. Due to this poor performance, many laboratories that have purchased this software have never used it for experiments. Analysis of EEG signals and epileptic activity is still largely done by manual observation, which is a slow, tedious, and highly-subjective process.

To a large extent, the approaches to seizure detection and classification have ignored another form of data—recorded video. While human observation of video images has its limitations, such as high subjectivity and high false-negative rates, progress in new technology such as digital video analysis suggests an alternative to EEG technology. A few video-EEG systems have been developed for both clinical use and research in animals. However, most of these video-EEG systems simply record both EEG signals and video for human review. The best these systems can do is display the EEG epileptiform and video images of the animal simultaneously on a screen while recording them for post-capture review. This is a subjective, time consuming, inefficient, and expensive process. It is likely that subtle seizures will be missed during rapid manual review of recorded video alone.

SUMMARY OF THE INVENTION

A system for detecting animal seizure behavior includes a module configured to analyze video images of an animal to detect and classify seizure behavior of the animal. In one embodiment, the module comprises an animal identification module configured to segregate images of the animal from the video images, a posture and body part identification module configured to identify a posture of the animal as one of a set of predetermined postures and identify at least one body part of the animal, a seizure-salient feature detection module configured to detect seizure-salient features using the identified postures and at least one body part of the animal, and a seizure detection and classification module configured to detect and classify occurrences of seizure behavior in the video images using the seizure-salient features. The system may also include a behavior identification module configured to identify a behavior of the animal as one of a set of predetermined behaviors.

A method for detecting animal seizure behavior includes segregating images of an animal from video images, identifying a posture of the animal as one of a set of predetermined postures, identifying at least one body part of the animal, detecting seizure-salient features using the identified posture and at least one body part, and detecting and classifying occurrences of seizures using the seizure-salient features. The method may also include identifying a behavior of the animal as one of a set of predetermined behaviors.

In one embodiment, the seizure-salient features include a Tail Raise feature, a Lordotic Posture feature, a Forelimb Clonus feature, an Overall Body Motion feature, a Bounding Box feature, and a Rearing feature.

DETAILED DESCRIPTION

Figure 1:
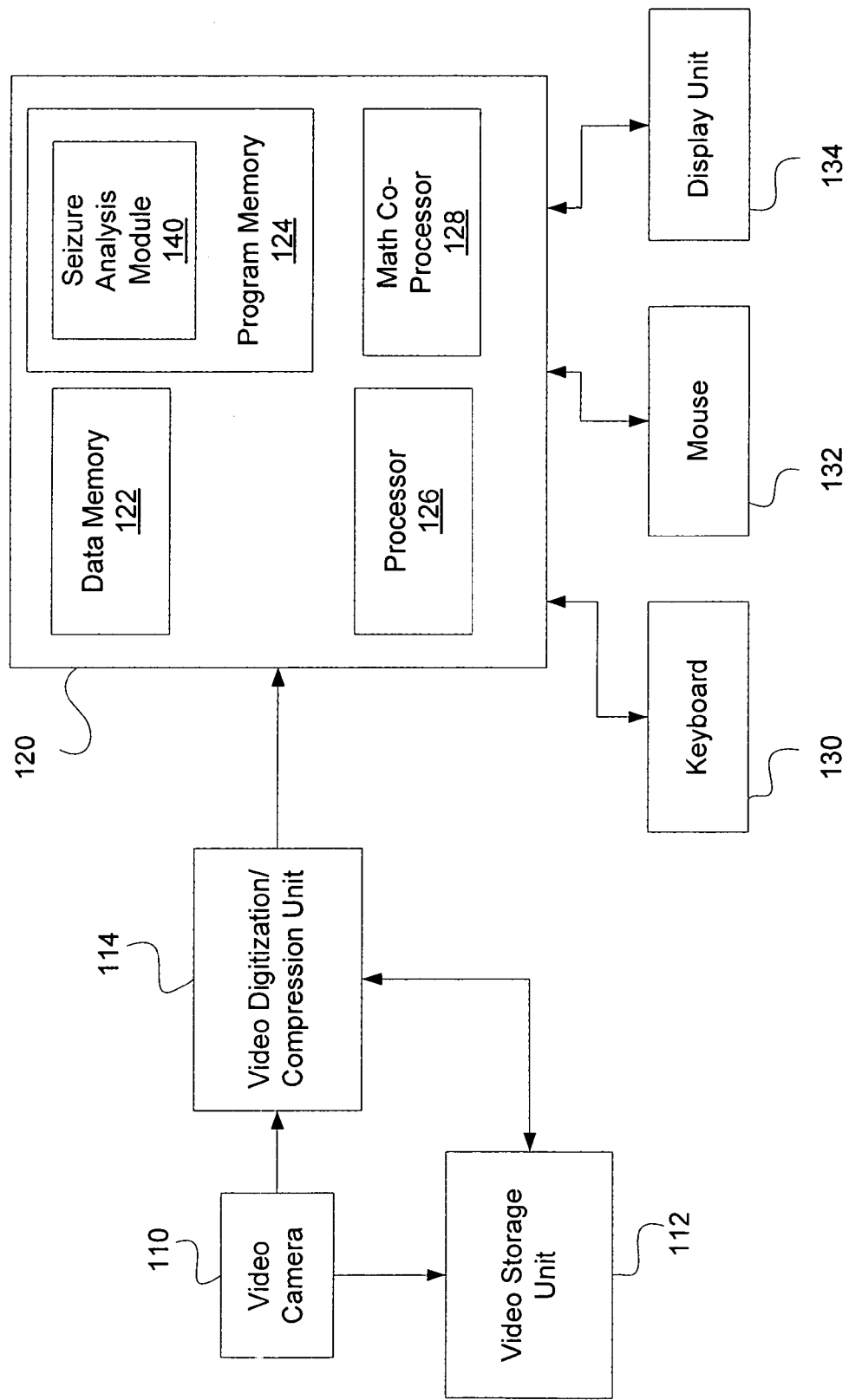
FIG. 1 is a block diagram of one embodiment of a system for detection and classification of seizures in animals, in accordance with the invention.

FIG. 1 is a block diagram of a system 100, including but not limited to, a video camera 110, a video storage unit 112, a video digitization/compression unit 114, a computer 120, a keyboard 130, a computer mouse 132, and a display unit 134. Video camera 110 can provide captured analog or digital video images to video storage unit 112 and/or video digitization/compression unit 114. The video images are typically formatted at 30 frames per second. Video digitization/compression unit 114 receives real-time video images from video camera 110 or stored video images from video storage unit 112, and digitizes analog video images and compresses digital video images. Video storage unit 112 may be implemented as any type of storage device, for example a computer hard-drive, CD, or DVD.

Computer 120 includes, but is not limited to, a data memory 122, for example a RAM or other type of non-volatile or volatile memory, a program memory 124, for example a hard drive or other type of non-volatile or volatile memory, a processor 126, and a math co-processor 128. Computer 120 may also include a video processor such as an MPEG coder/decoder (not shown). Computer 120 receives compressed digital video images from video digitization/compression unit 114. Program memory 124 includes, but is not limited to, a seizure analysis module 140.

Figure 2:
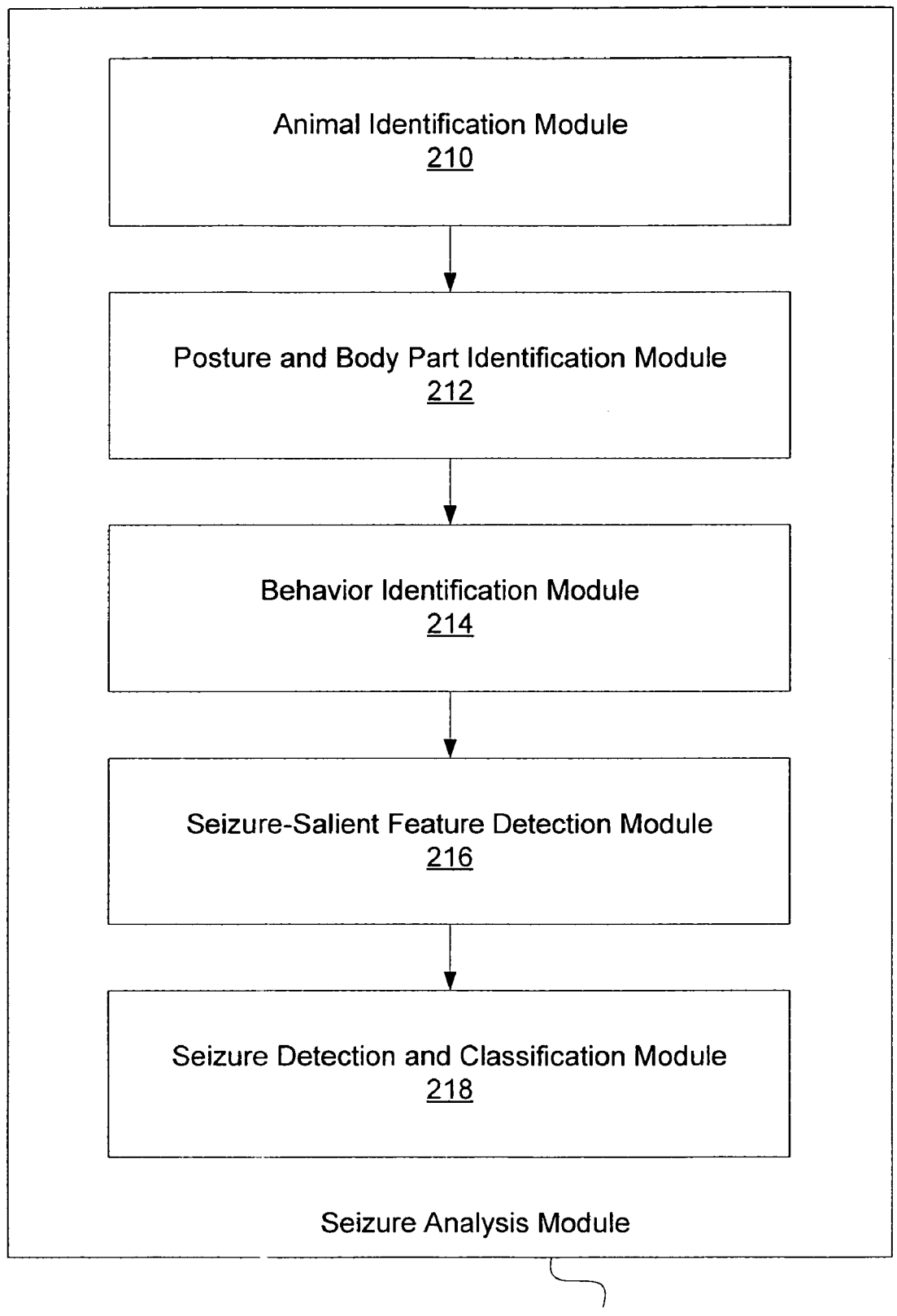
FIG. 2 is a block diagram of the seizure analysis module of FIG. 1.
Figure 6A:
FIG. 6A is a video frame showing a side view of a rat having a seizure.
Figure 6B:
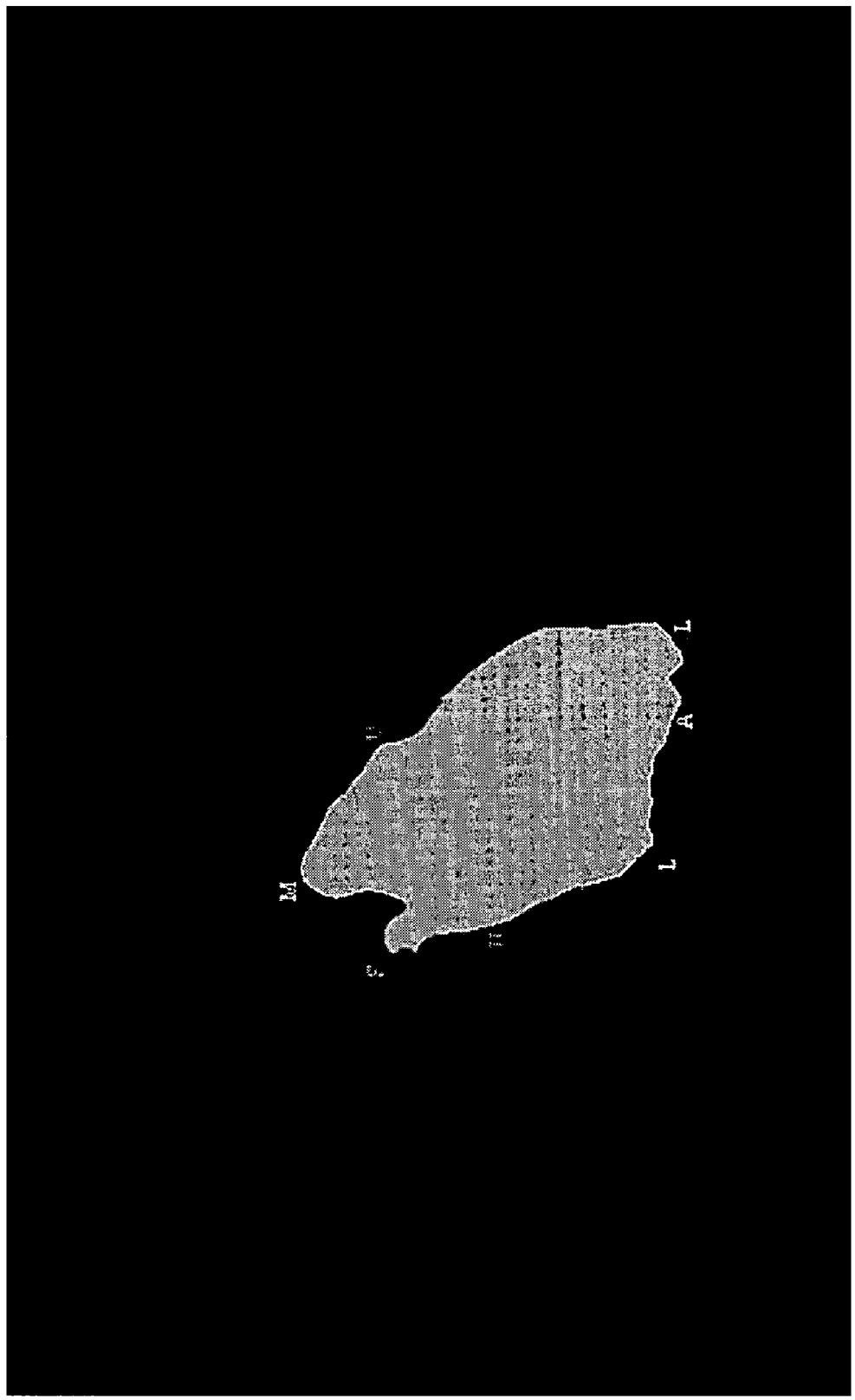
FIG. 6B is a video frame showing the extracted foreground image of FIG. 7A.

FIG. 2 is a block diagram of seizure analysis module 140 of FIG. 1, including but not limited to, an animal identification module 210, a posture and body part identification module 212, a behavior identification module 214, a seizure-salient feature calculation module 216, and a seizure detection and classification module 218. Animal identification module 210 identifies and segregates a predetermined type of object (an animal) from each input frame of digital video. An exemplary output of module 210 is shown in FIG. 6A. Animal identification module 210 may use any appropriate method to identify and segregate the image of the animal from each input frame, for example background subtraction, mixture modeling, or robust estimation. Posture and body part identification module 212 identifies a current posture of the animal and identifies the various body parts of the animal.

Behavior identification module 214 identifies the behavior of the animal over a series of video frames as one of a set of predetermined behaviors. The behavior identification is input to seizure-salient feature detection module 216, which detects all the features that can distinctly identify the occurrence of a seizure. These features are further discussed below. The seizure-salient features are input to seizure detection and classification module 218, which detects and classifies all occurrences of seizures and calculates seizure parameters such as seizure type, number of occurrences, duration, and frequency.

Figure 3:
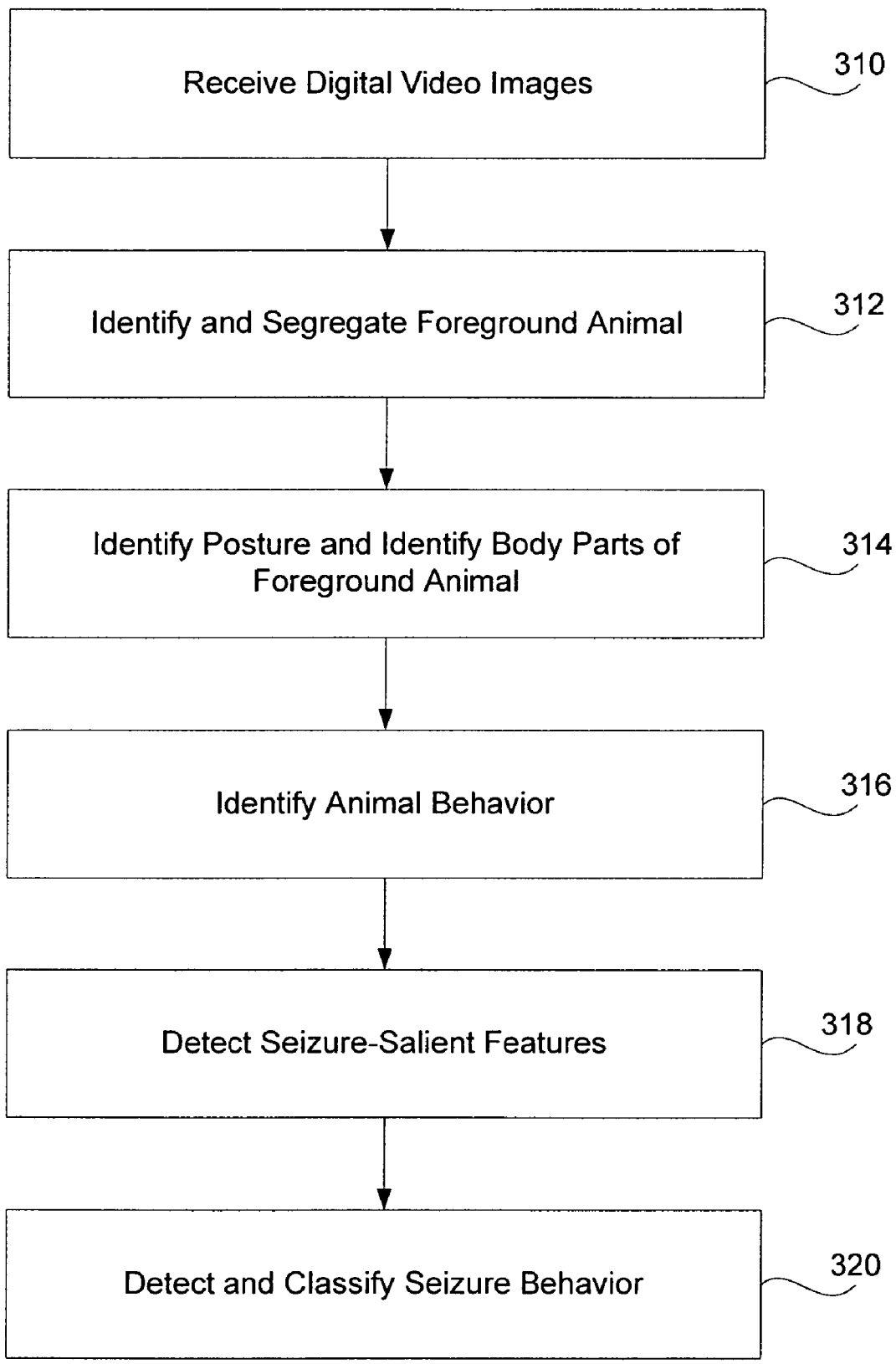
FIG. 3 is a flowchart of method steps for detecting and classifying seizure behavior in animals, in accordance with one embodiment of the invention.

FIG. 3 is a flowchart of method steps for detecting and classifying animal seizure activity, in accordance with one embodiment of the invention. In step 310, seizure analysis module 140 receives digital video frames of an animal. In step 312, animal identification module 210 identifies and segregates the animal from each received video frame. In an exemplary embodiment, animal identification module 210 uses a background subtraction technique. A pre-generated background frame for the received video frames is used to determine foreground objects by determining the intensity differences between the background frame and each received video frame and applying a threshold procedure to remove noise. A labeling procedure may be used to screen out disconnected small noisy regions and improve the region that corresponds to the animal. In the labeling procedure, all pixels in a frame will be assigned a label as a foreground pixel or a background pixel based on a predetermined threshold. The foreground pixels are further cleaned up by removing smaller components and leaving only the largest component as the foreground animal. Foreground pixels that border a background pixel form the contour of the animal.

Figure 4A:
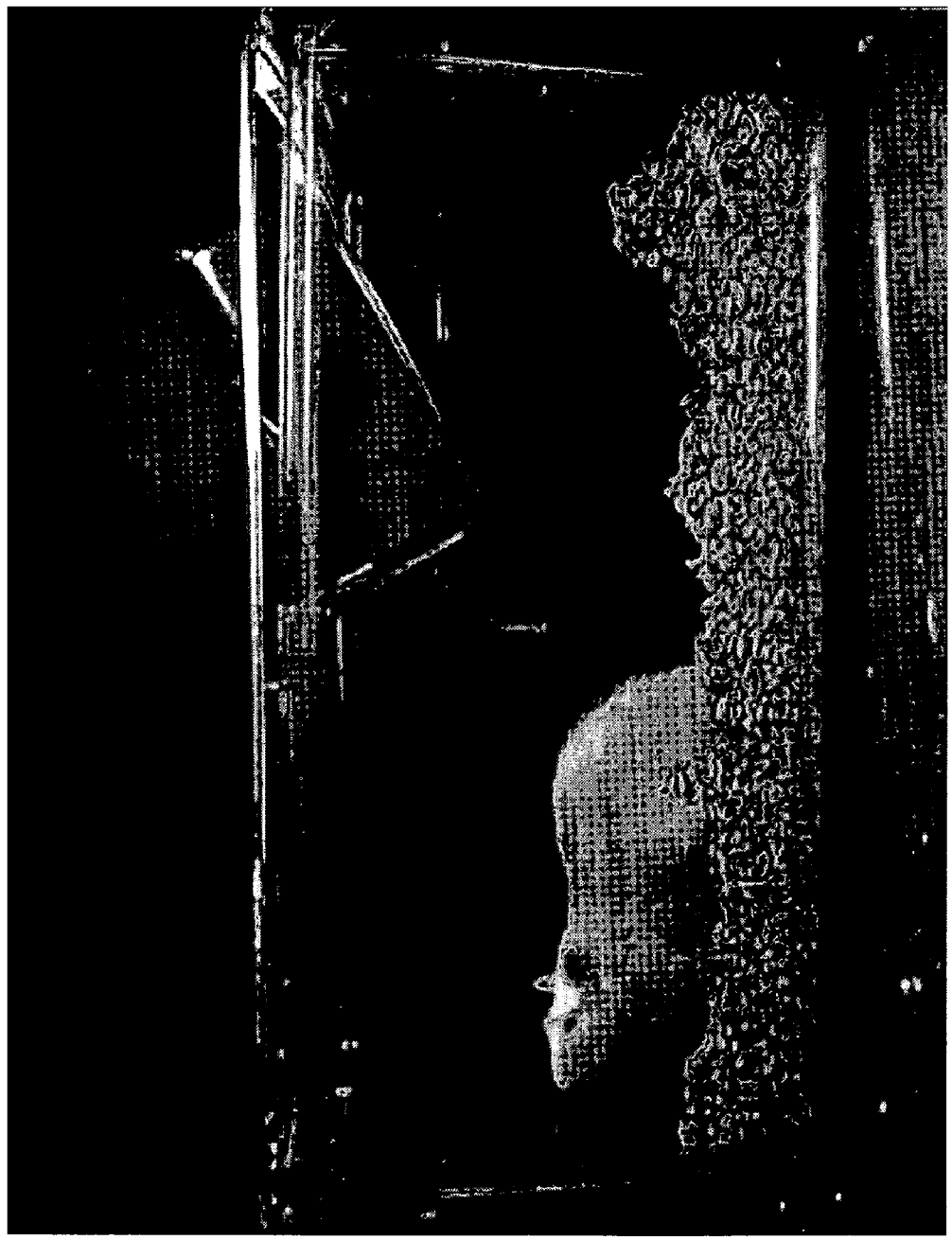
FIG. 4A is a exemplary video frame showing a side view of a rat in a cage.
Figure 4B:
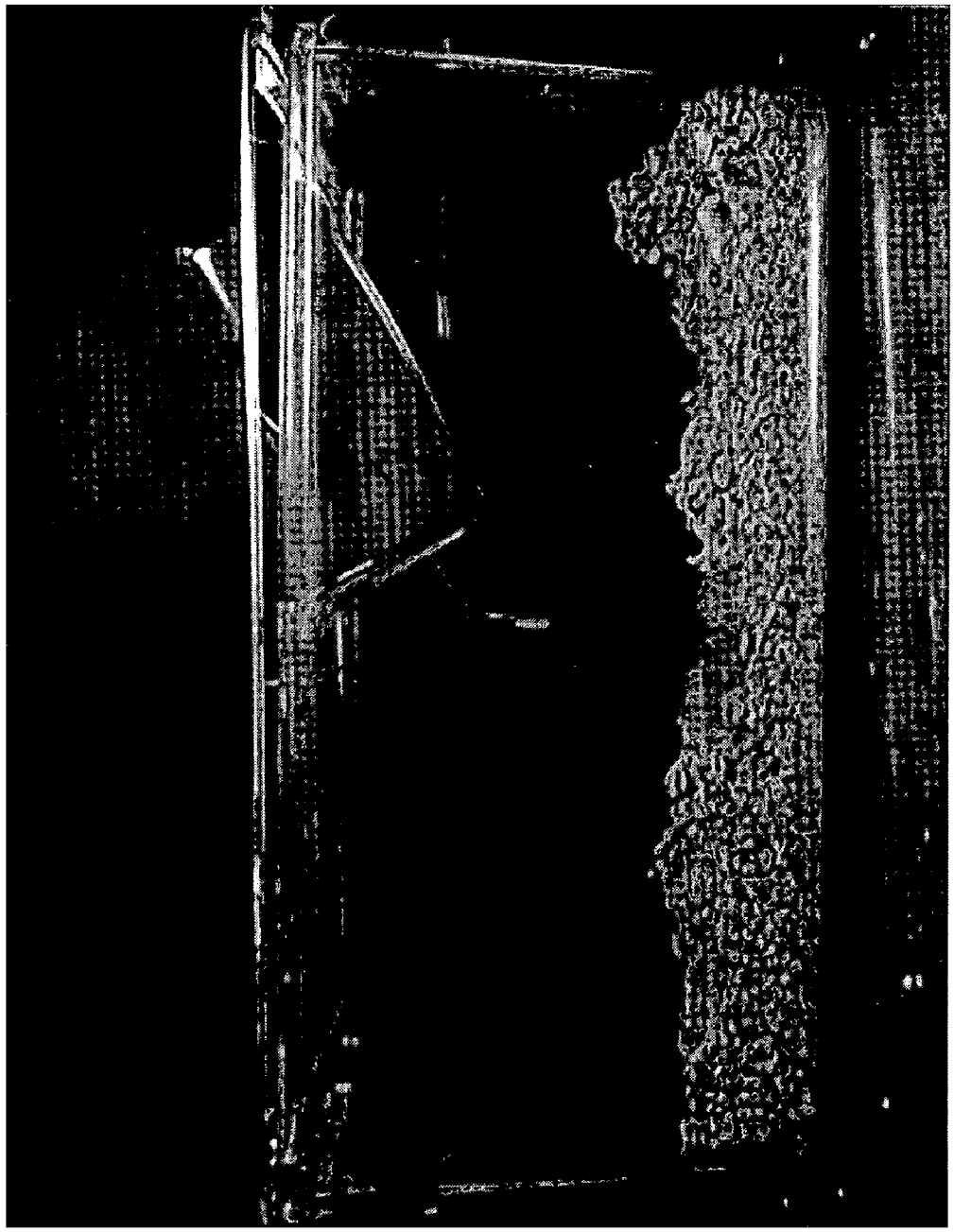
FIG. 4B is a background image of the frame of FIG. 5A without the rat.
Figure 5A:
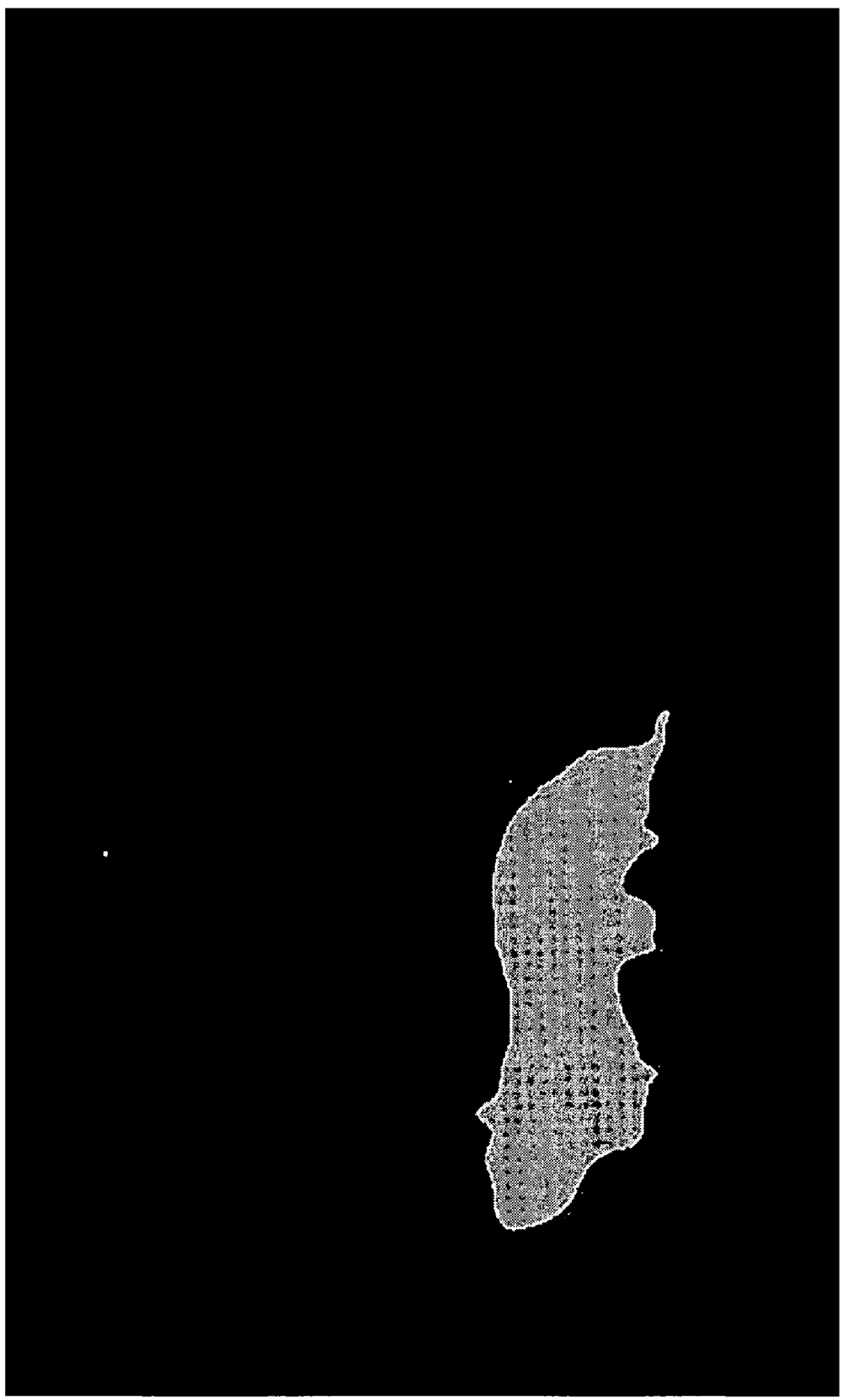
FIG. 5A is a video frame showing an extracted foreground image of an animal.

FIG. 4A shows an original video frame and FIG. 4B shows a pre-generated background frame for the series of video frames. FIG. 5A shows the detected foreground image frame that results from the identification and segregation of the animal from the video image of FIG. 4A.

Returning to FIG. 3, in step 314 the posture and body part identification module 212 identifies a current posture of the animal for each video frame and identifies the body parts of the animal for each video frame. Module 212 first calculates position features of the animal including the centroid, principal orientation angle, area (number of pixels), eccentricity (roundness), and the aspect ratio of the animal with lengths measured along the primary and secondary axes of the animal. These position features are calculated as follows:

S is the set of pixels of the foreground frame, A is the area in number of pixels, $(C_x, C_y)$ is the centroid, $\phi$ is the orientation angle, E is the eccentricity, and R is the aspect ratio.

$$C_x = \frac{1}{A}\sum_S x$$

$$C_y = \frac{1}{A}\sum_S y$$

Three intermediate terms, called second order moments, are defined as:

$$m_{2,0} = \sum_S (x - C_x)^2$$

$$m_{0,2} = \sum_S (y - C_y)^2$$

$$m_{1,1} = \sum_S (x - C_x)(y - C_y)$$

Using the central moments:

$$\phi = \frac{1}{2}\arctan\frac{2m_{1,1}}{m_{2,0} - m_{0,2}}$$

$$E = \frac{(m_{2,0} - m_{0,2})^2 + 4m_{1,1}^2}{(m_{2,0} + m_{0,2})^2}$$

R is equal to the ratio of the length of the range of the points projected along an axis perpendicular to $\phi$ to the length of the range of the points projected along an axis parallel to $\phi$. This may also be defined as the aspect ratio (ratio of width to length) after rotating the foreground object by $\phi$.

Module 212 then uses the calculated position features to identify the current posture of the animal as one of a set of predetermined postures. In one embodiment, the set of predetermined postures includes:

1. Horizontally positioned, side view, normal or elongated
2. Vertically positioned, rearing or hanging
3. Cuddled-up
4. Horizontally positioned, front or back view (axis along viewer's line of sight)
5. Partially reared
6. Stretched or elongated
7. Hang Vertical (hanging from the top of the cage)
8. Hang Cuddled (hanging from top of cage with all four limbs).

In one embodiment, module 212 uses a decision tree classifier trained to identify a posture based on the calculated position features. The decision tree classifier was trained with video images for which postures were manually classified. Other types of classifiers are within the scope of the invention.

Figure 5B:
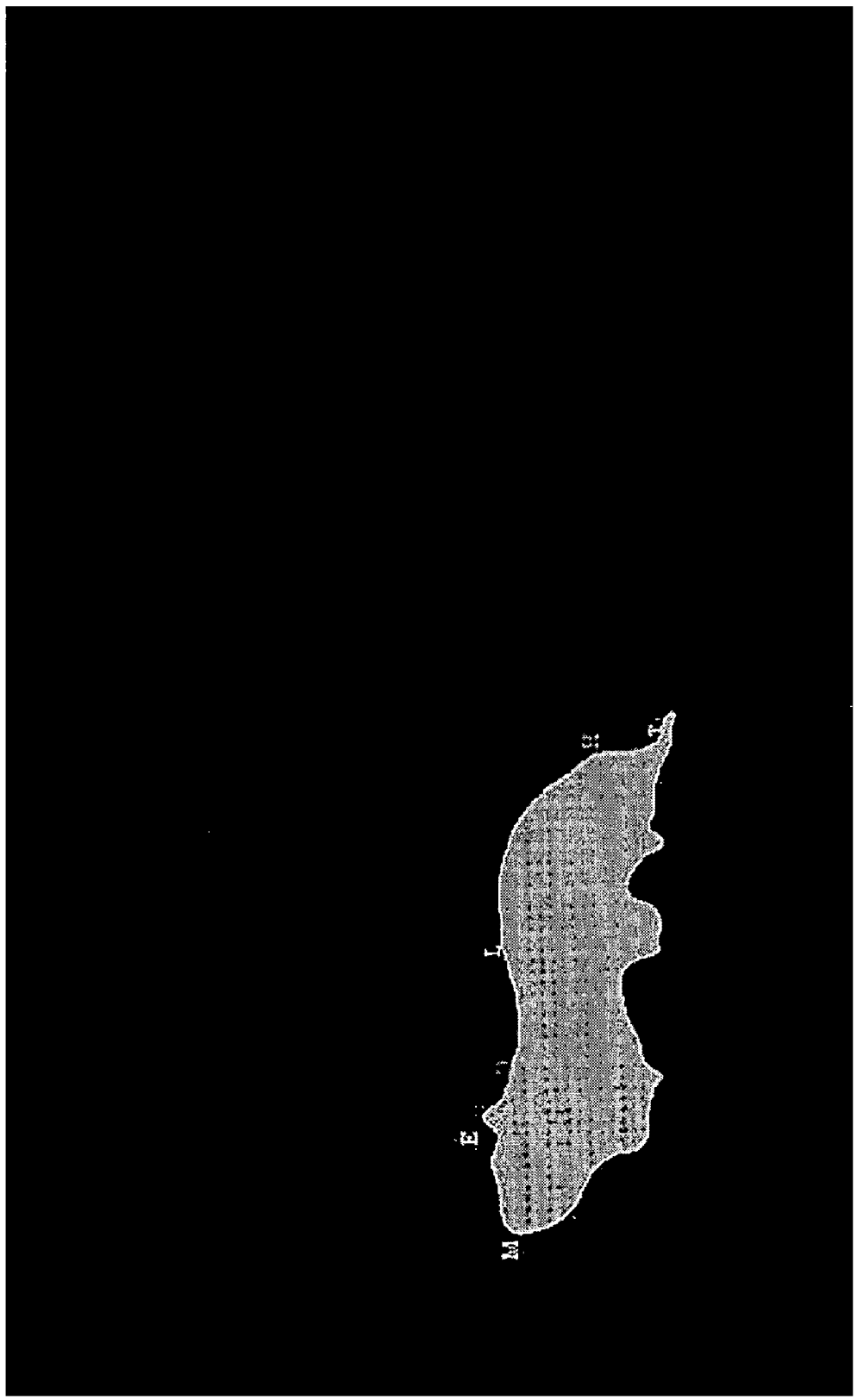
FIG. 5B is a video frame of the extracted foreground image of FIG. 6A with contour segments of the outline of the whole animal body labeled.

After identifying the posture of the animal, module 212 identifies the body parts of the animal. The outline contour of the whole body of the animal is divided into segments that are classified as body parts. In one embodiment, the outline contour of the animal is smoothed and analyzed to determine convex and concave extremes of curvature. The outline contour is divided such that each contour segment starts at one concave point, goes through one convex point, and ends at the next concave point. Module 212 then analyzes the contour segments to determine segment features including segment length, mean and variance of curvature, average thickness of the body over the segment, and orientation of the midpoint of the segment from the centroid of the animal. Module 212 then classifies each of the contour segments as a body part based on the segment features. In one embodiment, module 212 uses a decision tree classifier trained to identify body parts based on segment features. Other types of classifiers are within the scope of the invention. The decision tree classifier identifies each contour segment as one of a predetermined set of body parts, including for example head/mouth, ear, upper back, lower back, abdomen, hind limb, forelimb, and tail. FIG. 5B shows an example of an outline contour of an animal divided into body parts.

Next, in step 316, behavior identification module 214 identifies the behavior of the animal based on a series of identified postures. Module 214 identifies the current behavior of the animal as one of a set of predetermined behaviors, including but not limited to, sleep, sniff, groom, eat, rear up on hind legs, come down, drink, walk, jump, hang from top of cage, stretch, dig, awaken, twitch, yawn, pause, circle, forage, chew, and urinate. In one embodiment, module 214 uses Hidden Markov Models (HMMs) to identify behaviors based on a sequence of posture labels. The HMMs were trained using sequences of posture labels manually classified as behaviors. Other types of statistical models are within the scope of the invention. Some of the above-listed behaviors can be very similar to seizure behaviors, so these non-seizure behaviors are identified first and seizure-salient features from these behaviors are used to detect seizure behaviors. Normal walking or other locomotion activities can be falsely identified as seizure behaviors, so when these behaviors are detected seizure-salient detection module 216 does not process the corresponding image data for seizure-salient features.

In step 318, seizure-salient feature detection module 216 detects seizure-salient features using the identified postures and behaviors of the animal. Seizure-salient features for a rat include, but are not limited to, Tail Raise, Lordotic Posture, Rearing, Forelimb Clonus, Overall Body Motion, and Bounding Box. Different animals may have different types of seizure-salient features.

A. Tail Raise

Figure 7:
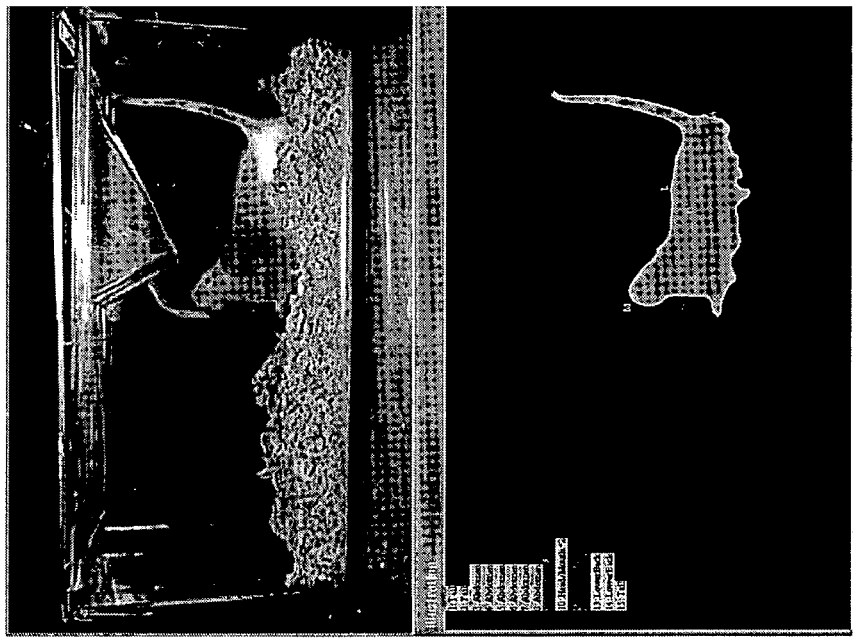
FIG. 7 shows two video frames of a rat exhibiting an exemplary seizure-salient feature, the Tail Raise.

A rat's tail can become stiff and raised up during the entire duration of a seizure. Although the rat raises its tail during other behaviors such as urination, the raised tail during a seizure is usually accompanied by a very taut tail. The Tail Raise seizure-salient feature is detected by identifying the rat's tail and measuring its angle relative to the rest of the body and its orientation. A slight knot or twist of the tail may occur in the raised tail. This knot travels up the raised tail from the tail base to the tail tip slowly. FIG. 7 illustrates a rat exhibiting the Tail Raise seizure-salient feature.

Module 216 median filters the Tail Raise feature over a window of 15 frames centered at the current frame. Noise is easily filtered out and only when the Tail Raise feature is TRUE for a substantially long period will this generate a TRUE value contribution. Let the value of the Tail Raise feature at frame i be represented by $TR_i$. Then, $$TR_i = \begin{cases} 1, & \text{if Tail Raise is TRUE} \\ 0, & \text{if Tail Raise is FALSE} \end{cases}$$

B. Lordotic Posture

Figure 8B:
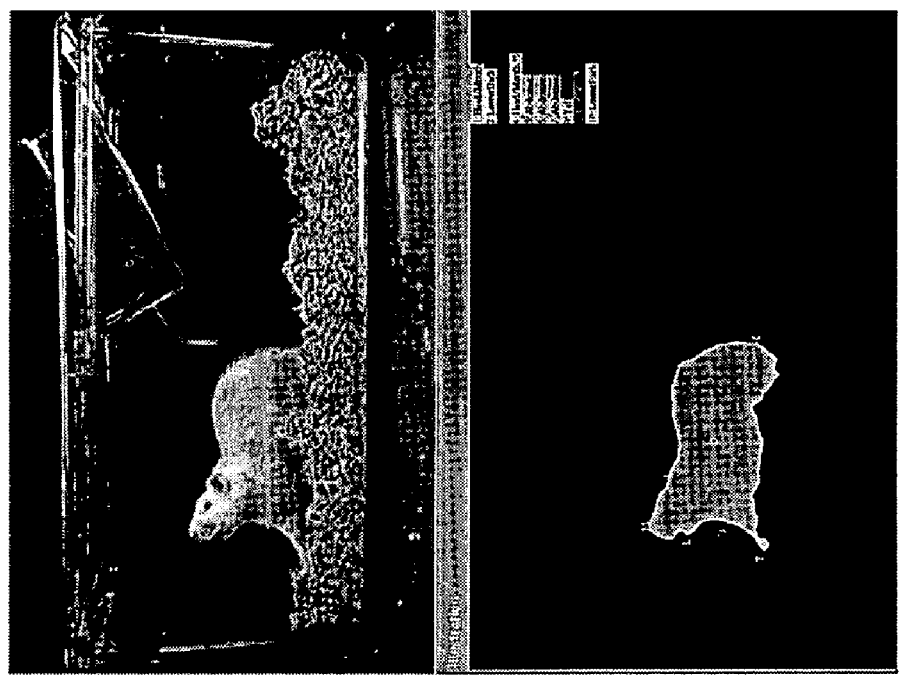
FIG. 8B shows two video frames of a rat exhibiting a Lordotic Posture.
Figure 8A:
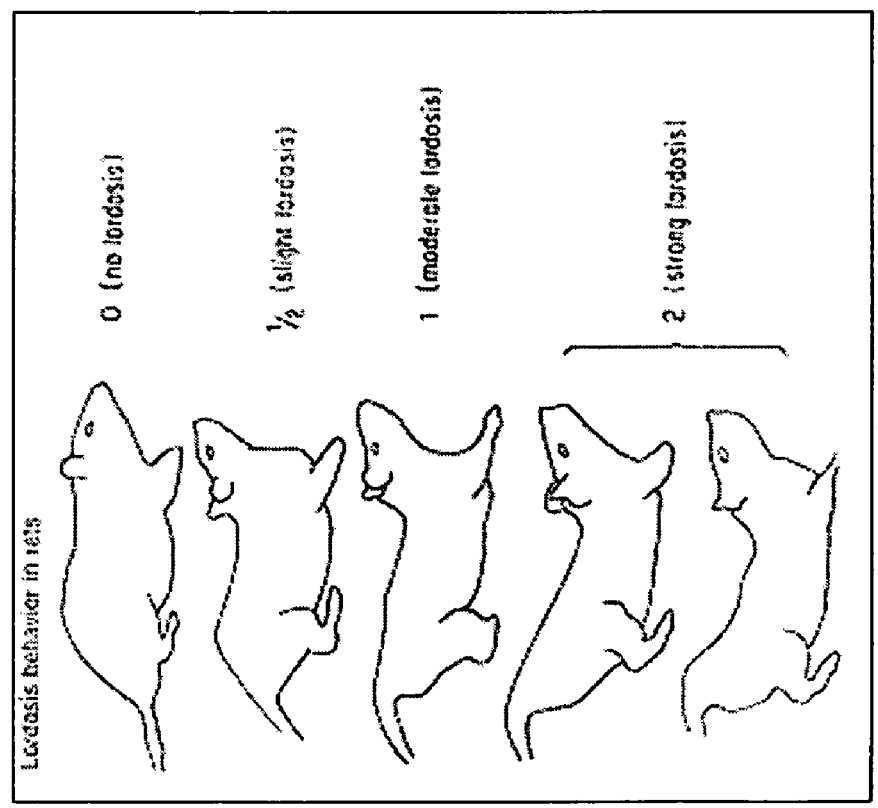
FIG. 8A is an illustration of another exemplary seizure-salient feature, Lordotic Posture.

During a seizure, a rat may exhibit a Lordotic Posture, or lordosis. The Lordotic Posture is also exhibited in other specialized behaviors like mating behaviors. The Lordotic Posture is characterized by a deep valley in the contour of the rat's upper back and the tip of the head/mouth pointing up. FIG. 8A is a diagram showing various degrees of lordosis. In one embodiment, module 216 applies a set of rules to each identified posture and if the rules are satisfied, the Lordotic Posture is detected. FIG. 8B show a video image and a foreground image in which a rat is exhibiting a slight to moderate Lordotic Posture during a seizure.

Similar to the Tail Raise feature, the Lordotic Posture feature is TRUE when seizure-salient detection module 216 detects that the animal is in a lordotic posture. After median filtering the Lordotic Posture feature over a window of 15 frames centered at the current frame, seizure behavior and detection module 218 calculates the value of this feature at frame i, represented by $LP_i$, as $$LP_i = \begin{cases} 1, & \text{if Lordotic Posture is TRUE} \\ 0, & \text{if Lordotic Posture is FALSE} \end{cases}$$

C. Forelimb Clonus

Figure 9:
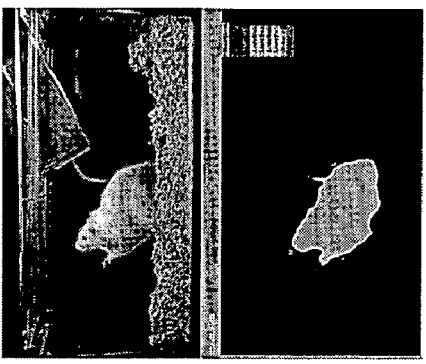
FIG. 9 shows a series of video frames of a rat exhibiting another seizure-salient feature, Forelimb Clonus.
Figure 9:
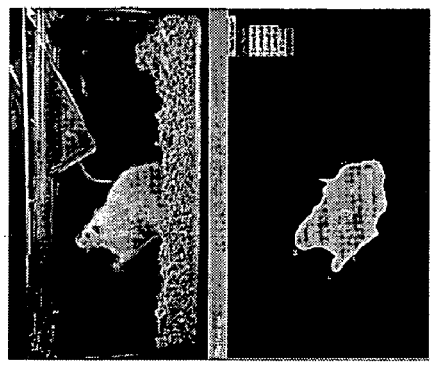
Figure 9:
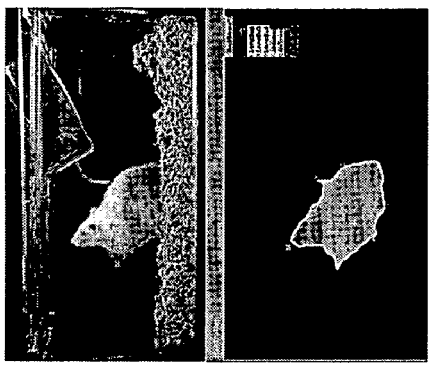
Figure 9:
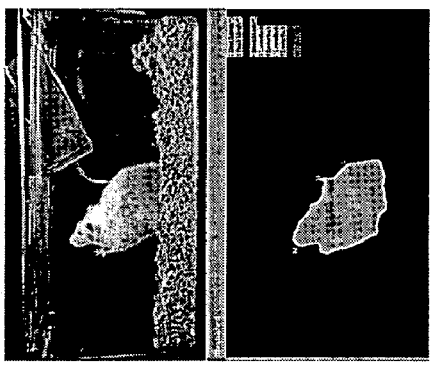
Figure 9:
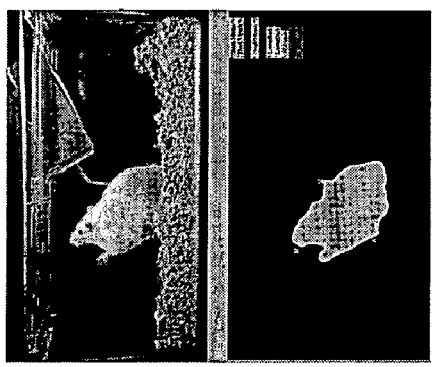
Figure 9:
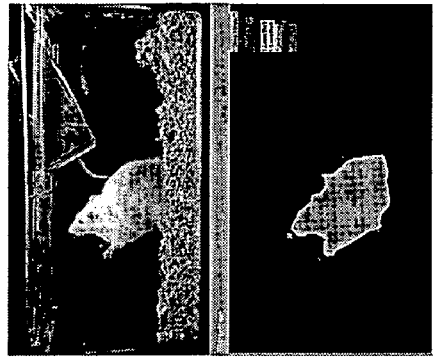

The Forelimb Clonus feature is the most indicative of the occurrence of a seizure. The Forelimb Clonus feature is detected when the amount of forelimb motion from one video frame to the next exceeds a predetermined threshold. The forelimb of the animal is identified by posture and body part identification module 212 in step 314. In step 318, seizure-salient feature detection module 216 determines the relative motion of the pixels of the forelimb segment by calculating the average displacement of the pixels from one video frame to the next. For each pixel in the forelimb segment, module 216 determines the closest distance to a pixel in the next video frame and determines the mean distance over all pixels in the forelimb segment, producing a forelimb motion metric that represents the magnitude of forelimb movement. If the forelimb motion metric exceeds a predetermined threshold, the Forelimb Clonus feature is detected. FIG. 9 shows a series of six video frames during a seizure showing a full cycle of Forelimb Clonus.

For the Forelimb Clonus feature, module 216 calculates the forelimb motion metric for each frame (this value is 0 if there are no forelimbs detected in a frame), and smooths it using the median filter. Let this smoothed value of the forelimb motion metric at frame i be $FLM_i$. Then, module 216 calculates the Forelimb Clonus feature at frame i, represented by $FC_i$, as $$FC_i = \begin{cases} 1, & \text{if } FLM_i > T_{FCLow} \\ -1, & \text{otherwise} \end{cases}$$

where $T_{FCLow}$ is the threshold for the $FLM_i$. Note that there is a negative feedback when no forelimb motion is present. This negative feedback offsets any noise from other features and helps to keep the false positive rate low.

D. Overall Body Motion

During a seizure, the entire animal's body may exhibit violent convulsions. An Overall Body Motion feature is detected when the amount of motion of the entire body of the animal is between two predetermined thresholds. Seizure-salient feature detection module 216 determines the average closest distance per pixel over all pixels of the contour of the animal, producing a body motion metric that represents the amount of deformation of the entire body contour of the animal from one frame to the next. Normal walking or other locomotive behavior results in bodily deformations that have a high body motion metric. Thus, the Overall Body Motion seizure-salient feature is detected when the value of the body motion metric is higher than a low predetermined threshold and lower than a high predetermined threshold.

For the Overall Body Motion feature, module 216 calculates the total body motion metric for each frame, and smooths it using the median filter. Let this smoothed value of the total body motion metric at frame i be $TBM_i$. Then, module 216 calculates the Overall Body Motion feature at frame i, represented by $BM_i$, as $$BM_i = \begin{cases} 1, & \text{if } T_{TBLow} < TBM_i < T_{TBHigh} \\ -1, & \text{otherwise} \end{cases}$$

where $T_{TBLow}$ and $T_{TBHigh}$ are the low and high motion thresholds. Note again that a negative feedback is produced either when there is little or no motion of the entire body at all, or if there is too much motion as occurs while the animal is walking.

E. Bounding Box

Convulsive activity of an animal experiencing a seizure results in periodic deformation of the entire body contour of the animal. Seizure-salient feature detection module 216 detects this convulsive activity by measuring the movement of the sides of a rectangular bounding box around the entire body contour of the animal as a bounding box shift metric. Module 216 also calculates a sum of the changes of the sides of the bounding box from frame to frame.

Module 216 calculates the bounding box shift metric, and smooths it with the median filter. Let the smoothed value at frame i be represented by $BBS_i$, then, the bounding box feature, represented by $BB_i$, is calculated as, $$BB_i = \begin{cases} 1, & \text{if } BBS_i > T_{BBLow} \\ 0, & \text{otherwise} \end{cases}$$

where $T_{BBLOW}$ is the threshold for the bounding box shift metric.

F. Rearing

Rearing by itself is a normal behavior and is only used as a seizure-salient feature when at least one other seizure-salient feature is detected. The Rearing feature is also used to classify the type of seizure.

The Rearing feature is used as a positive indicator only when at least one of the other features is positive. For each frame i, if any of $TR_i$, $LP_i$, $FC_i$, $BM_i$, or $BB_i$ is greater than 0, and if the animal posture in that frame is Reared Up Posture, the Rearing feature for that frame i is 1. Module 216 smooths this feature using the median filter, and if the smoothed value is 1, the Rearing posture feature $RP_i$ for frame i is 1, otherwise, it is 0.

G. Other Features

Other optional seizure-salient features can be detected by seizure-salient detection module 216. For example, a Chewing Motion feature can be detected. During a seizure, an animal's mouth may open and close as if it is chewing a hard-to-chew item. If the view is head-on, the Chewing Motion feature is detected by measuring the amount of the darker pixels corresponding to the open mouth region and measuring the fluctuation of this amount. If the view is side-on, the Chewing Motion feature is detected by measuring the curvature near the tip of the mouth and measuring the fluctuation in the concavity near the tip corresponding to the open mouth.

Returning to FIG. 3, in step 318 seizure detection and classification module 218 uses the detected seizure-salient features to detect and classify the occurrence of a seizure. All of the seizure-salient features may or may not occur during a seizure, so module 218 uses a combination of the seizure-salient features to generate a final indicator of the seizure. Module 218 calculates an epilepsy signal for each video frame using a value for each of the seizure-salient features. Module 218 analyzes the epilepsy signal over time (i.e.; a series of video frames) to calculate a range where a seizure is occurring.

The total epilepsy signal $ES_i$ at frame i is calculated by, $$ES_i = TR_i + LP_i + FC_i + BM + BB_i + RP_i$$

If the $ES_i$ value is less than 1, module 218 sets it to 0. Any value that is greater than 0 is considered as a possible signal for the occurrence of a seizure. Weights $w_j$ can be added to each of the seizure-salient feature components to adjust the relative contributions of these features to the total signal. In one embodiment, these weights are all equal to 1.

Obviously, most seizures last for several seconds. Hence, module 218 post-processes this ES data by first removing noise spikes that are too short to be of any significance using a simple initial threshold operation on the length of a continuous sequence of positive ES values. In one embodiment, this initial length threshold is predetermined as 10. So, module 218 immediately discards any sequence of positive ES values that are 10 or fewer frames long, leaving only sequences of positive ES values that are greater than 10 frames long. Next, module 218 merges any of these sequences of continuous positive ES values that are separated by a small gap, the combination limit, to generate larger sequences of possible seizures. In one embodiment, this combination limit is predetermined as 10. Finally, module 218 applies a final length threshold on these larger combined sequences. In one embodiment, the final length threshold is predetermined as 60 frames (or 2 seconds). Any post-merge sequences that are 60 or fewer frames long are also discarded and hence, post-processing produces a final set of detected seizures that are at least 2 seconds long. The user of seizure analysis module 140 is able to change the predetermined values of the initial length threshold, the combination limit, and the final length threshold.

In addition to detecting the occurrence of seizures, seizure detection and classification module 218 classifies the type of seizure. Seizures are classified according to their severity on a scale of P1 to P5, with P1 being the least severe and P5 being the most severe. Type P1 and P2 seizures exhibit very subtle behaviors that are difficult to detect via analysis of video, thus the following discussion focuses on type P3 to P5 seizures.

A type P3 seizure occurs when the animal repeatedly raises and lowers its forelimbs in a paddling or swimming motion, along with rapid head jerking movements. A type P4 seizure occurs when the paddling motion of both forelimbs and the rapid head jerking occurs while the animal is reared up on its hind limbs. A type P4 seizure is often observed as the animal sits up and "paddles," or as the animal vigorously climbs along the walls of the cage. A type P5 seizure occurs when the animal falls over as a result of the previously described seizure behaviors. A seizure can begin abruptly as type P4 or P5, or it can progress in severity from a type P3 seizure.

If a seizure is detected and no Rear Up behavior is detected during the seizure, module 218 classifies the seizure as type P3. If a seizure is detected and a Rear Up behavior is detected during the seizure, module 218 classifies the seizure as type P4. If a seizure is detected and a Come Down behavior is detected following a Rear Up behavior, module 218 classifies the seizure as a type P5 since the Come Down behavior is very similar to the animal falling over.

Figure 10:
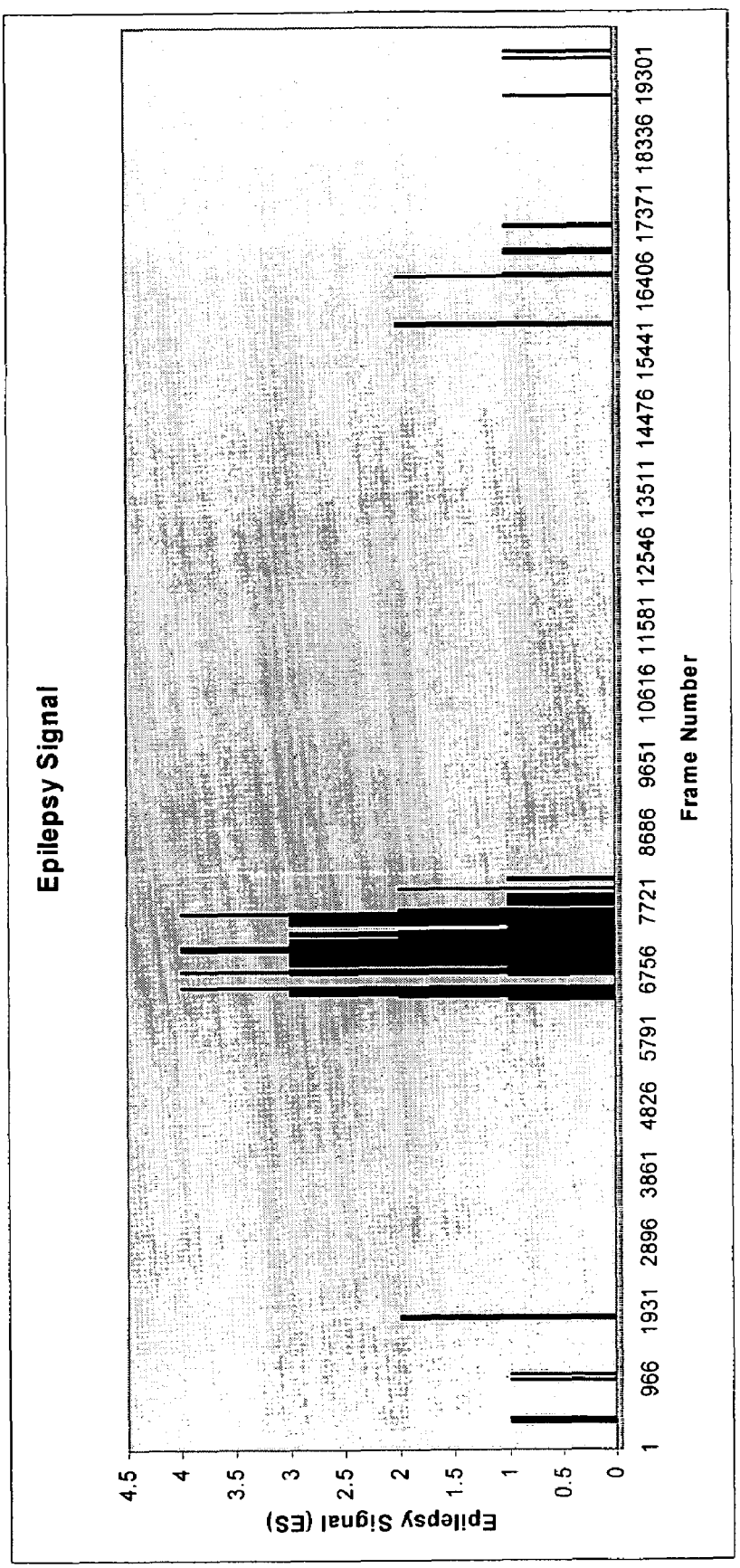
FIG. 10 is a plot of an exemplary seizure signal, in accordance with one embodiment of the invention.

FIG. 10 is a plot of an exemplary epilepsy signal ES. Only a 20000-frame segment (corresponding to a little over 11 minutes of video) of a 2-hour video is shown. A manual observation of this video segment detected one fairly long seizure from frame 6266 to 7588. Seizure detection and classification module 218 generated the plot shown in FIG. 10 for this 20000-frame segment. The section of dense spikes approximately from frame 6400 to 7700 is the range that matches this seizure. Module 218 detects a type P5 seizure between frames 6330-6430, another type P5 seizure between frames 6752-7131, another type P5 seizure between frames 7162-7317, a type P4 seizure between frames 7472-7545, and finally another type P5 seizure between frames 7702-7824. Module 218 will tend to divide up the entire approximately 1300 frame seizure, identified by a human observer as a single seizure bout, into several smaller components of the large bout. This occurs due to some of the noise filtering that is applied to remove small sub-10 frame sequences and the inability to combine adjacent ranges. Moreover, during certain portions of the seizure all features might not be visible. Sometimes, there would also be certain truly "quiet periods" in the middle of a seizure. But, humans are much better able to use context to bridge gaps and generate long bouts. The last detected type P5 seizure from frame 7702-7824 is a false positive that was identified because the animal did some jerky movements after the seizure seemed to have ended, that resembled seizure-like movements. Occasional occurrences of these false positives cannot be avoided. The noise spikes that are present towards the left and right ends of the plots are easily discarded by the noise filtering approach using the minimum length thresholds.

In addition to generating a plot like that shown in FIG. 10, seizure detection and classification module 218 also generates parameters of the detected seizures to the user. These parameters include, but are not limited to, the number of occurrences of each type of seizure, the percentage of total experiment time that these individual types of seizures occurred, and the frequency of the occurrence. This information may be output in a text file, in a statistical software format such as Systat and SPSS, or in a spreadsheet software format.

Figure 11:
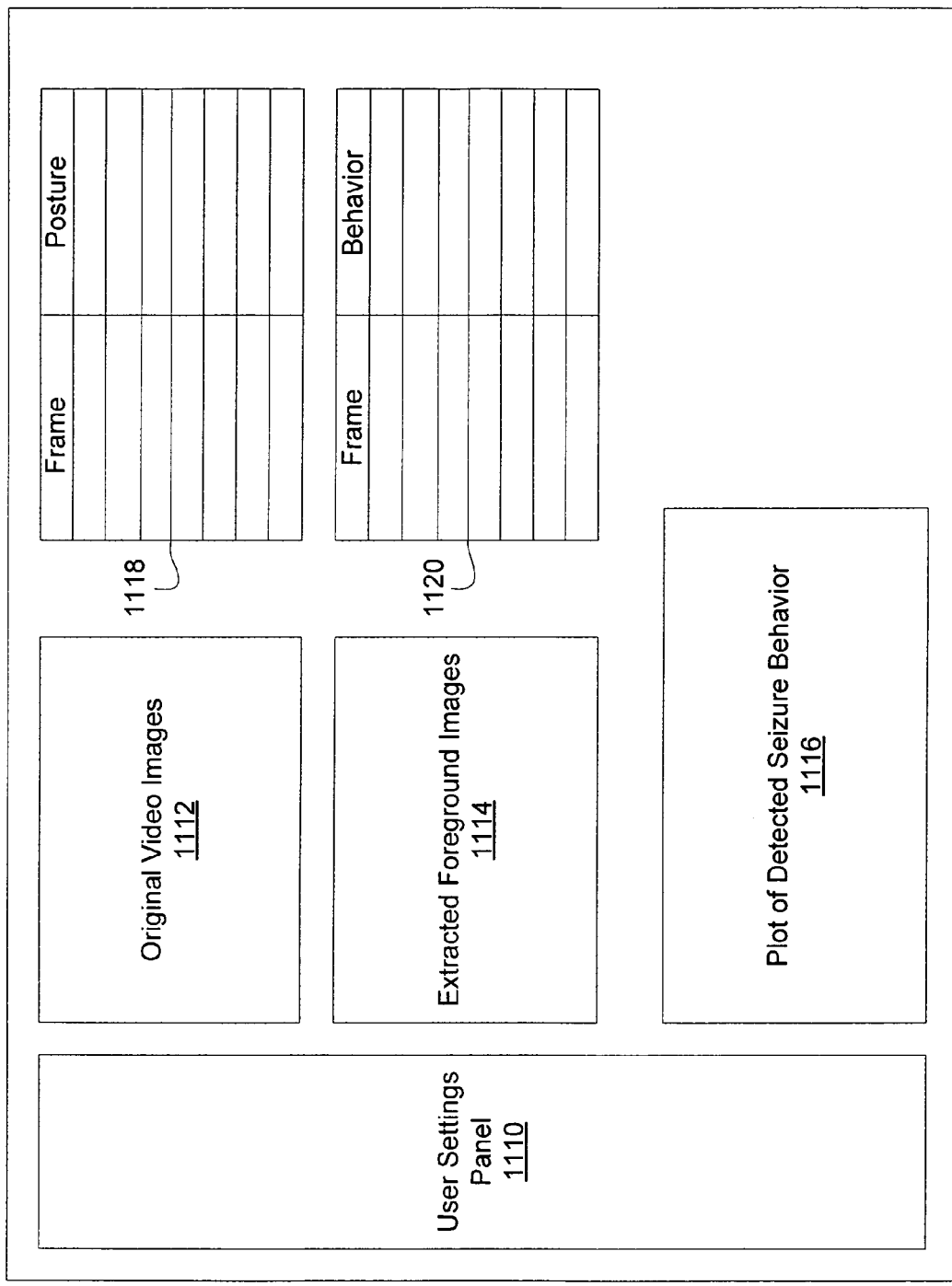
FIG. 11 is a diagram of one embodiment of the output of the seizure analysis module of FIG. 1 as displayed to a user, in accordance with the invention.

FIG. 11 is a diagram of one embodiment of the output of the seizure analysis module 140 as displayed to a user. Display 1100 includes, but is not limited to, a user settings panel 1110, an original video images panel 1112, an extracted foreground images panel 1114, a plot of seizure behavior panel 1116, a frame and posture table 1118, and a frame and behavior table 1120. Original video images panel 1112 shows a playback of the original video images being analyzed by seizure analysis module 140. Extracted foreground images panel 1114 shows the images of the extracted foreground animal generated by animal identification module 210. An example of an extracted foreground image is shown in FIG. 5A. Extracted foreground images panel 1114 alternately may show images of the extracted foreground animal with the body contour segments labeled. Plot of seizure behavior panel 1116 shows the value of the epilepsy signal ES as it is calculated for each frame of video by seizure detection and classification module 218. Frame and posture table 1118 shows a table of the frame number and the identified posture for that frame for each frame of the video being analyzed. Frame and behavior table 1120 shows a table of the frame number and the identified behavior for that frame for each frame of the video being analyzed. User setting panel 1110 is a graphical user interface that allows a user to change various settings for video analysis module 140. Although a certain arrangement of panels is shown in FIG. 11, any arrangement of the panels is within the scope of the invention.

The invention has been described above with reference to specific embodiments. It will, however, be evident that various modifications and changes may be made thereto without departing from the broader spirit and scope of the invention as set forth in the appended claims. The foregoing description and drawings are, accordingly, to be regarded in an illustrative rather than a restrictive sense.

What is claimed is:

1. A system for detecting animal seizure behavior, comprising:
a seizure analysis module implementable by a processor configured to analyze video images including images of an animal to detect and classify seizure behavior of the animal,
wherein the seizure analysis module comprises:
an animal identification module configured to segregate images of the animal from the video images;
a posture and body part identification module configured to identify a posture of the animal as one of a set of predetermined postures and to identify at least one body part of the animal;
a seizure-salient feature detection module configured to detect at least one of seizure-salient features using the posture and the at least one body part of the animal; and
a seizure detection and classification module configured to detect and classify occurrences of seizure behavior in the video images using the seizure-salient features and to calculate seizure parameters, including a type of seizure.

2. The system of claim 1, further comprising a behavior identification module configured to identify a behavior of the animal as one of a set of predetermined behaviors.

3. The system of claim 1, wherein the seizure-salient features include a Tail Raise feature.

4. The system of claim 1, wherein the seizure-salient features include a Lordotic Posture feature.

5. The system of claim 1, wherein the seizure-salient features include a Forelimb Clonus feature.

6. The system of claim 1, wherein the seizure-salient features include an Overall Body Motion feature.

7. The system of claim 1, wherein the seizure-salient features include a Bounding Box feature.

8. The system of claim 1, wherein the seizure-salient features include a Rearing feature.

9. The system of claim 1, wherein the seizure-salient features include a Chewing Motion feature.

10. The system of claim 1, wherein the type of seizure is a type P3, a type P4, or a type P5.

11. The system of claim 1, wherein the animal is a mouse.

12. The system of claim 1, wherein the animal is a rat.

13. A method for detecting animal seizure behavior, the method comprising:
acquiring video image data of an animal;
electronically communicating the video image data to a seizure analysis module;
segregating one or more images of the animal from the video image data using the seizure analysis module;
identifying using the seizure analysis module at least one posture of the animal as one of a set of postures based on the segregated one or more images of the animal;
identifying using the seizure analysis module at least one body part of the animal based on the segregated one or more images of the animal;
detecting using the seizure analysis module at least one seizure-salient feature of the animal using the at least one identified posture and the at least one body part of the animal; and
detecting and classifying using the seizure analysis module occurrences of one or more seizures using the at least one detected seizure-salient feature, comprising calculating seizure parameters, including classifying a detected seizure as a type of seizure;
whereing at least the steps of image segregation, posture identification, body part identification, and seizure detection are implementable by a processor.

14. The method of claim 13, further comprising identifying a behavior of the animal as one of a set of predetermined behaviors using a behavior identification module.

15. The method of claim 13, wherein the seizure-salient features include a Tail Raise feature.

16. The method of claim 13, wherein the seizure-salient features include a Lordotic Posture feature.

17. The method of claim 13, wherein the seizure-salient features include a Forelimb Clonus feature.

18. The method of claim 13, wherein the seizure-salient features include an Overall Body Motion feature.

19. The method of claim 13, wherein the seizure-salient features include a Bounding Box feature.

20. The method of claim 13, wherein the seizure-salient features include a Rearing feature.

21. The method of claim 13, wherein the seizure-salient features include a Chewing Motion feature.

22. The method of claim 13, wherein the type of seizure is a type P3, a type P4, or a type P5.

23. The method of claim 13, wherein the animal is a mouse.

24. The method of claim 13, wherein the animal is a rat.

25. A computer-readable medium comprising instructions for detecting animal seizure behavior by:
acquiring video images of an animal;
segregating images of the animal from the video images;
identifying at least one posture of the animal as one of a set of predetermined postures using the segregated images of the animal;
identifying at least one body part of the animal using the segregated images of the animal;
detecting at least one of seizure-salient features of the animal using the at least one posture and the at least one body part of the animal; and
detecting and classifying occurrences of seizures using the seizure-salient features, comprising calculating seizure parameters, including classifying a detected seizure as a type of seizure;
wherein at least the steps of image segregation, posture identification, body part identification, and seizure detection are implementable by a processor.

26. The computer-readable medium of claim 25, further comprising instructions for:
   identifying a behavior of the animal as one of a set of predetermined behaviors.

27. The computer-readable medium of claim 25, wherein the seizure-salient features include a Tail Raise feature.

28. The computer-readable medium of claim 25, wherein the seizure-salient features include a Lordotic Posture feature.

29. The computer-readable medium of claim 25, wherein the seizure-salient features include a Forelimb Clonus feature.

30. The computer-readable medium of claim 25, wherein the seizure-salient features include an Overall Body Motion feature.

31. The computer-readable medium of claim 25, wherein the seizure-salient features include a Bounding Box feature.

32. The computer-readable medium of claim 25, wherein the seizure-salient features include a Rearing feature.

33. The computer-readable medium of claim 25, wherein the seizure-salient features include a Chewing Motion feature.

34. The method of claim 13 further comprising:
   displaying the video image including the image of the animal;
   displaying an extracted foreground image of the animal;
   displaying a table comprising a frame number and the posture of the animal identified for that frame;
   displaying a table comprising a frame number and the behavior of the animal identified for that frame; and
   displaying a plot of the detected seizure behavior.

35. The method of claim 34, further comprising displaying a user settings graphical user interface.

36. The method of claim 34, wherein the extracted foreground image of the animal includes labels for body parts of the animal.

* * * * *

UNITED STATES PATENT AND TRADEMARK OFFICE
CERTIFICATE OF CORRECTION

PATENT NO. : 7,643,655 B2  Page 1 of 1
APPLICATION NO. : 11/329573
DATED : January 5, 2010
INVENTOR(S) : Liang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 908 days.

Signed and Sealed this

Sixteenth Day of November, 2010

David J. Kappos
*Director of the United States Patent and Trademark Office*